(12) United States Patent
Kahook

(10) Patent No.: US 10,004,635 B2
(45) Date of Patent: Jun. 26, 2018

(54) NASOLACRIMAL IMPLANTS AND RELATED METHODS FOR TEAR STIMULATION

(71) Applicant: The Regents of the University of Colorado, a body corporate, Denver, CO (US)

(72) Inventor: Malik Y. Kahook, Denver, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 100 days.

(21) Appl. No.: 15/345,765

(22) Filed: Nov. 8, 2016

(65) Prior Publication Data

US 2017/0049619 A1 Feb. 23, 2017

Related U.S. Application Data

(62) Division of application No. 15/180,451, filed on Jun. 13, 2016.

(Continued)

(51) Int. Cl.
*A61N 1/36* (2006.01)
*A61N 1/372* (2006.01)
(Continued)

(52) U.S. Cl.
CPC .......... *A61F 9/0017* (2013.01); *A61F 9/0026* (2013.01); *A61F 9/00772* (2013.01);
(Continued)

(58) Field of Classification Search
CPC .. A61F 9/0017; A61F 9/00772; A61F 9/0026; A61N 1/0551; A61N 1/36046;
(Continued)

(56) References Cited

U.S. PATENT DOCUMENTS 3,949,750 A 4/1976 Freeman
4,745,100 A 5/1988 Gilbard et al.
(Continued)

FOREIGN PATENT DOCUMENTS

WO WO 98/18459 5/1998
WO WO 2012/068247 A1 5/2012
(Continued)

OTHER PUBLICATIONS

Aggarwal, H., et al., "Evaluation of the Effect of Transcutaneous Electrical Nerve Stimulation (TENS) on Whole Salivary Flow Rate," J. Clin Exp. Dent. 7(1), pp. e-13-e17 (2015).
(Continued)

*Primary Examiner* — Pamela M Bays
(74) *Attorney, Agent, or Firm* — Tarolli, Sundheim, Covell & Tummino LLP

(57) ABSTRACT

A device for inducing production of tears may include a body extending from a proximal end to a distal end. The body may be configured for insertion through a puncta of a subject. The device also may include a stimulus delivery mechanism positioned between the proximal end and the distal end and an induction coil operably coupled to the stimulus delivery mechanism. Further, the device may include an external controller wirelessly coupled to the induction coil for inductively transferring energy to the induction coil.

28 Claims, 8 Drawing Sheets

Related U.S. Application Data

(60) Provisional application No. 62/321,961, filed on Apr. 13, 2016, provisional application No. 62/180,265, filed on Jun. 16, 2015.

(51) Int. Cl.
| | |
|---|---|
| A61N 1/05 | (2006.01) |
| A61F 9/00 | (2006.01) |
| A61N 1/378 | (2006.01) |
| A61F 9/007 | (2006.01) |
| A61F 7/12 | (2006.01) |
| A61H 23/02 | (2006.01) |
| A61N 2/00 | (2006.01) |
| A61N 5/06 | (2006.01) |
| A61N 7/00 | (2006.01) |

(52) U.S. Cl.
CPC ........... *A61N 1/36* (2013.01); *A61N 1/36046* (2013.01); *A61N 1/3787* (2013.01); *A61N 1/37205* (2013.01); *A61N 1/37229* (2013.01); *A61F 7/12* (2013.01); *A61H 23/02* (2013.01); *A61N 1/0551* (2013.01); *A61N 1/36057* (2013.01); *A61N 1/37211* (2013.01); *A61N 2/004* (2013.01); *A61N 5/0603* (2013.01); *A61N 7/00* (2013.01); *A61N 2007/0004* (2013.01)

(58) Field of Classification Search
CPC .............. A61N 1/36057; A61N 1/3705; A61N 1/37211; A61N 1/37229; A61N 1/3787; A61N 1/37205; A61N 1/36
USPC .......................................................... 607/53
See application file for complete search history.

(56) References Cited

U.S. PATENT DOCUMENTS

| | | | |
|---|---|---|---|
| 4,951,683 | A | 8/1990 | Davis |
| 5,713,833 | A | 2/1998 | Milligan |
| 7,117,870 | B2 | 10/2006 | Prescott |
| 7,146,209 | B2 | 12/2006 | Gross et al. |
| 7,204,995 | B2 | 4/2007 | El-Sherif et al. |
| 7,247,623 | B2 | 7/2007 | Yerxa et al. |
| 7,981,095 | B2 | 7/2011 | Grennon et al. |
| 7,981,195 | B2 | 7/2011 | Korb et al. |
| 7,998,497 | B2 | 8/2011 | de Juan, Jr. et al. |
| 8,007,524 | B2 | 8/2011 | Korb et al. |
| 8,025,689 | B2 | 9/2011 | Korb et al. |
| 8,083,787 | B2 | 12/2011 | Korb et al. |
| 8,090,426 | B2 | 1/2012 | Felder |
| 8,128,673 | B2 | 3/2012 | Korb et al. |
| 8,128,674 | B2 | 3/2012 | Korb et al. |
| 8,137,390 | B2 | 3/2012 | Korb et al. |
| 8,201,562 | B2 | 6/2012 | Ordich |
| 8,210,902 | B2 | 7/2012 | Rapacki et al. |
| 8,333,726 | B2 | 12/2012 | Rapacki et al. |
| 8,364,232 | B2 | 1/2013 | Felder |
| 8,523,928 | B2 | 9/2013 | Korb et al. |
| 8,617,229 | B2 | 12/2013 | Korb et al. |
| 8,628,504 | B2 | 1/2014 | Grenon et al. |
| 8,632,578 | B2 | 1/2014 | Korb et al. |
| 8,685,073 | B2 | 4/2014 | Korb et al. |
| 8,691,265 | B2 | 4/2014 | de Juan, Jr. et al. |
| 8,702,643 | B2 | 4/2014 | Rapacki et al. |
| 8,747,884 | B2 | 6/2014 | de Juan, Jr. et al. |
| 8,795,711 | B2 | 8/2014 | de Juan, Jr. et al. |
| 8,918,181 | B2 | 12/2014 | Ackermann et al. |
| 8,950,405 | B2 | 2/2015 | Grenon et al. |
| 8,983,615 | B2 | 3/2015 | Tahmasian et al. |
| 8,996,137 | B2 | 3/2015 | Ackermann et al. |
| 9,011,361 | B2 | 4/2015 | de Juan, Jr. et al. |
| 9,095,723 | B2 | 8/2015 | Ackermann et al. |
| 9,132,088 | B2 | 9/2015 | Sim et al. |
| 9,149,643 | B2 | 10/2015 | Tahmasian et al. |
| 9,168,222 | B2 | 10/2015 | de Juan, Jr. et al. |
| 9,199,080 | B2 | 12/2015 | Gekeler et al. |
| 9,216,028 | B2 | 12/2015 | Korb et al. |
| 2002/0035358 | A1 | 3/2002 | Wang |
| 2002/0198573 | A1* | 12/2002 | Nisch ........................ A61F 2/14 607/54 |
| 2005/0197614 | A1 | 9/2005 | Pritchard et al. |
| 2006/0235367 | A1 | 10/2006 | Takashima et al. |
| 2007/0296487 | A1 | 11/2007 | de Juan, Jr. et al. |
| 2008/0038317 | A1 | 4/2008 | Chang et al. |
| 2008/0086101 | A1 | 4/2008 | Freilich |
| 2008/0103376 | A1* | 5/2008 | Felder ................ A61B 5/14532 600/347 |
| 2009/0092654 | A1 | 4/2009 | de Juan, Jr. et al. |
| 2009/0104248 | A1* | 4/2009 | Rapacki ................ A61F 9/0017 424/427 |
| 2009/0105749 | A1 | 4/2009 | de Juan, Jr. et al. |
| 2009/0240276 | A1 | 9/2009 | Ainpour et al. |
| 2010/0274204 | A1 | 10/2010 | Rapacki et al. |
| 2010/0274224 | A1 | 10/2010 | Jain et al. |
| 2010/0310622 | A1 | 12/2010 | Chauhan et al. |
| 2012/0245682 | A1 | 9/2012 | Rapacki et al. |
| 2013/0006326 | A1* | 1/2013 | Ackermann ....... A61N 1/36046 607/53 |
| 2013/0053733 | A1 | 2/2013 | Korb et al. |
| 2013/0172790 | A1 | 7/2013 | Badawi |
| 2013/0324908 | A1 | 12/2013 | Hong et al. |
| 2014/0066821 | A1 | 3/2014 | Friedland et al. |
| 2014/0161863 | A1 | 6/2014 | de Juan, Jr. et al. |
| 2014/0257433 | A1* | 9/2014 | Ackermann ....... A61N 1/37217 607/60 |
| 2014/0277429 | A1 | 9/2014 | Kuzma et al. |
| 2014/0316310 | A1 | 10/2014 | Ackermann et al. |
| 2014/0350376 | A1 | 11/2014 | Nachum |
| 2014/0371812 | A1 | 12/2014 | Ackermann et al. |
| 2015/0025545 | A1 | 1/2015 | Grenon et al. |
| 2015/0100063 | A1 | 4/2015 | Korb et al. |
| 2015/0157347 | A1 | 6/2015 | Grenon et al. |
| 2015/0224200 | A1 | 8/2015 | de Juan, Jr. et al. |
| 2015/0238754 | A1 | 8/2015 | Loudin et al. |
| 2015/0335900 | A1 | 11/2015 | Ackermann et al. |
| 2015/0351961 | A1 | 12/2015 | Kahook |
| 2015/0367037 | A1 | 12/2015 | Sim et al. |
| 2015/0374541 | A1 | 12/2015 | de Juan, Jr. et al. |
| 2016/0008171 | A1 | 1/2016 | de Juan, Jr. et al. |
| 2016/0022487 | A1 | 1/2016 | Lazar, Jr. |
| 2016/0022992 | A1 | 1/2016 | Franke et al. |

FOREIGN PATENT DOCUMENTS

| | | |
|---|---|---|
| WO | WO 2012/139063 A2 | 10/2012 |
| WO | WO 2014/172693 A2 | 10/2014 |

OTHER PUBLICATIONS

Fleisher, D, et al., "Improved Oral Drug Delivery: Solubility Limitations Overcome by the Use of Prodrugs," Adv. Drug Delivery Ref. 19(2), pp. 115-130 (1996).

Fujisawa, A., et al., "The Effect of Nasal Mucosal Stimulation on Schirmer Tests in Sjogren' Syndrome and Dry Eye Patients, in Lacrimal Gland, Tear Film, and Dry Eye Syndromes 3," pp. 1221-1226, Springer US (2002).

Haddrill, M., "Punctal Plugs for Dry Eyes," pp. 1-4, (2015).

Iwamoto, T., et al., "Ladcrimal Glands," Biomedical Foundations of Ophthalmology, vol. 1, Ch. 30, Harper & Row, Philadelphia (1982).

Newby, K., "A Real Tear-Jerker: Team Creates Device to Alleviate Dry Eye," Stanford Medicine News Center, pp. 1-7 (2015).

Ro, A.J. et al., "Morphological and Degradation Studies of Sirolimus-Containing Poly(Lactide-Co-Glycolide) Discs," Journal of Biomedical Materials Research Part B: Applied Biomaterials, 1006(3), pp. 767-777 (2012).

Tsubota, K., "Tear Dynamics and Dry Eye," Prog. Retin. Eye Res, 17(4), pp. 565-596 (1998).

Weber, W.P., "Smart Plug: The Intelligent Solution to Dry Eye," pp. 1-8 (2008).

(56) References Cited

OTHER PUBLICATIONS

Whitnall, S.E., "The Anatomy of the Human Orbit and Accessory Organs of Vision," $2^{nd}$ ed. pp. 208-252, Oxford University Press, London (1932).
Yang, W., et al., "Reservoir-Based Polymer Drug Delivery Systems," Journal of Laboratory Automation 17(1), pp. 50-58 (2012).
Yen, M.T., et al., "The Effect of Punctal Occlusion on Tear Production, Tear Clearance, and Ocular Surface Sensation in Normal Subjects," Am. J. Ophthalmol. 131(3), pp. 314-323 (2001).
International Search Report and Written Opinion in International Application No. PCT/US2016/037167, dated Sep. 1, 2016 (14 pages).

\* cited by examiner

NASOLACRIMAL IMPLANTS AND RELATED METHODS FOR TEAR STIMULATION

CROSS-REFERENCE TO RELATED APPLICATIONS

This application is a divisional of U.S. application Ser. No. 15/180,451, filed Jun. 13, 2016, which claims the benefits of priority to U.S. Provisional Application No. 62/321,961, filed Apr. 13, 2016, and U.S. Provisional Application No. 62/180,265, filed Jun. 16, 2015, each of which is incorporated by reference herein in its entirety.

TECHNICAL FIELD

Various aspects of the present disclosure relate generally to medical systems, devices, and related methods. More specifically, the present disclosure relates to devices, systems, and methods for performing therapies within a subject for the inducement of tear production via, e.g., nasolacrimal tissue stimulation.

BACKGROUND

Dry Eye Disease ("DED") is a condition that affects millions of people worldwide. The etiology of DED is becoming increasingly well understood. DED is progressive in nature, and results from the disruption of the natural tear film on the surface of the eye (e.g., the ocular surface). Such disruption may prevent healthy gas exchange and nutrient transport for the ocular surface, promote cellular desiccation, and/or may create a poor refractive surface for vision. The disruption of the natural tear film typically results from one or more of 1) insufficient aqueous tear production from the lacrimal glands (e.g., caused by secondary to post-menopausal hormonal deficiency, auto-immune disease, LASIK surgery, etc.), and/or 2) excessive evaporation of aqueous tears resulting from dysfunction of the meibomian glands. Low tear volume may cause a hyperosmolar environment that may induce an inflamed state of the ocular surface. This inflammatory response may induce apoptosis of ocular surface cells which in turn prevent proper distribution of the tear film on the ocular surface. Accordingly, any available tear volume delivered to the ocular surface may be rendered less effective. This may initiate a vicious cycle in which more inflammation can ensue, causing more ocular surface cell damage, etc. Additionally, the neural control loop, which controls reflex tear activation, may be disrupted because the sensory neurons in the ocular surface are damaged. As a result, fewer tears may be secreted and a second vicious cycle may develop that results in further progression of the disease (e.g., fewer tears may cause nerve cell loss, which may result in even fewer tears, etc.)

DED can result in ocular discomfort, visual disturbance, and/or a reduction in vision-related quality of life. Activities such as, e.g., driving, computer use, housework, and reading are often negatively impacted by DED. Subjects with severe cases of DED are at risk for serious ocular health deficiencies such as, e.g., corneal ulceration, and can experience a quality of life deficiency comparable to that of moderate to severe angina.

There is a wide spectrum of treatments for DED including: artificial tear substitutes, ointments, gels, warm compresses, environmental modification, topical cyclosporine, omega-3 fatty acid supplements, punctal plugs, moisture chamber goggles, punctal cautery, systemic cholinergic agonists, systemic anti-inflammatory agents, mucolytic agents, autologous serum tears, PROSE scleral contact lenses, and tarsorrhaphy. While current treatment options for DED are numerous, such treatment options have limited effectiveness and generally provide only mild symptom relief or improvement in ocular health over a short period of time.

The systems, devices, and methods of the current disclosure may rectify some of the deficiencies described above or address other aspects of the prior art.

SUMMARY

Aspects of the present disclosure relate to, among other things, nasolacrimal tissue stimulation. Each of the examples disclosed herein may include one or more the features described in connection with any of the other disclosed examples.

In one example, a device for inducing production of tears may include a body extending from a proximal end to a distal end. The body may be configured for insertion through a puncta of a subject. Additionally, the device may include a stimulus delivery mechanism positioned between the proximal end and the distal end.

Examples of the device may additionally include one or more of the following features. The stimulus delivery mechanism may include a conductor. The device may additionally include a plurality of conductors positioned between the proximal end and the distal end of the body. An induction coil may be operably coupled to the stimulus delivery mechanism. The body may be configured for direct contact with a canaliculus of a subject. The device may further include a faceplate adjacent the proximal end of the body. The device may further include a sensor configured for sensing one or more of biochemical properties of tears, placement of the body, and operation of stimulus delivery mechanism.

In one example, a device for inducing production of tears may include a body extending from a proximal end to a distal end. The body may be configured for insertion through a puncta of a subject. The device also may include a stimulus delivery mechanism positioned between the proximal end and the distal end and an induction coil operably coupled to the stimulus delivery mechanism. Further, the device may include an external controller wirelessly coupled to the induction coil for inductively transferring energy to the induction coil.

Examples of the device may additionally include one or more of the following features. The body may include an opening extending through a side wall of the body. At least a portion of the stimulus delivery mechanism may be positioned within the opening. The body may include a plurality of openings extending through a side wall of the body. The stimulus delivery mechanism may include a conductor. A plurality of conductors may be positioned between the proximal end and the distal end of the body. A faceplate may be adjacent the proximal end of the body. The faceplate may have a faceplate diameter larger than a diameter of the proximal end of the body. The induction coil may be in direct contact with the faceplate. The body and the faceplate may include non-planar surfaces. The body may be tapered such that the proximal end may have a proximal end diameter and the distal end may have a distal end diameter, and the distal end diameter may be smaller than the proximal end diameter. A lumen may extend from the proximal end of the body to the distal end of the body. The body may include mesh. The mesh may be self-expandable. A sensor may be configured for sensing one or more of biochemical properties of tears, placement of the body, and operation of stimulus delivery mechanism.

In a further example, a method for inducing production of tears may include contacting tissue of a canaliculus of a subject with a stimulus delivery mechanism of a device. The method may further include wirelessly communicating a stimulation signal from an external device to an induction coil associated with the device. Further, the method may include stimulating tissue of the canaliculus of the subject via the stimulation delivery mechanism to induce tearing from a lacrimal gland of the subject.

Examples of the method may additionally include one or more of the following features. Additionally, the method may include inserting the device through a puncta of the subject and positioning the device within the canaliculus of the subject. Upon inserting the device and positioning the device, no portion of the device may be received within a nasal cavity of the subject. Stimulating tissue of the canaliculus of the subject may include exciting at least one of the nasociliary nerve, the supratrochlear nerve, and the infratrochlear nerve to induce tearing from the lacrimal gland of the subject.

In a further example, a system for inducing production of tears may include a plurality of stimulation devices. Each stimulation device may include a body extending from a proximal end to a distal end, a stimulus delivery mechanism positioned between the proximal end and the distal end, and an induction coil operably coupled to the stimulus delivery mechanism. The system also may include an external controller wirelessly coupled to the induction coil of each of the plurality of stimulation devices for inductively transferring energy to the induction coil. Further, the placement of at least one stimulation device of the plurality of stimulation devices may be dependent on the placement of at least one other stimulation device of the plurality of stimulation devices.

In a further example, at least one device for stimulating the lacrimal system may include a stimulator body having at least one power source and a control subsystem with a distal end bio-stimulus transducer in electronic communication with the control subsystem. The control subsystem may include at least logic and communication circuits. The at least one device may include a proximal end faceplate. The faceplate may include at least one sensor and at least one antenna in electronic communication with the control subsystem.

Additionally, the at least one device may include one or more of the following features. The stimulator body may further include an isolation coupling between the control subsystem and the bio-stimulus transducer. The power source may include a battery. The logic and communication circuits may receive specific stimulus programming instructions through the antenna. The antenna may provide a wireless link between the control subsystem and at least one wireless device. The wireless device may include a computer, a smartphone, a tablet, a smart watch, or the like. The medical device may be controlled through the wireless device through a program application or "app." The battery may be rechargeable. The isolation coupling may be a vibration-dampening element. The control subsystem may further include memory to store operational data from the stimulator and configured to retrieve data from the antenna. The sensors may evaluate conductivity. The sensor may be a molecular sensor. The sensor may be a biological sensor. The antenna may be a communication antenna. The antenna may further include a radio frequency (RF) power amplifier.

At least the distal end of the device may include a flexible outer stimulator body. The stimulator body may include an expandable component. The stimulator body may include a helical outer wall. The helical outer wall may be configured to expand vertically. The helical outer wall may be configured as a horizontal anchor. The stimulus transducer may further include multiple zones comprising electrodes. The electrical stimulation may include a biphasic pulse waveform. The biphasic pulse waveform may be symmetrical. The frequency of the biphasic pulse waveform may be between about 20 Hz and about 80 Hz. The stimulator body may further include at least one distal end magnetic component. The stimulator body may further include at least one distal end magnetic component with magnetic attraction to a second device. The second device may include another stimulator device. The bio-stimulus transducer may include at least one vibration element. The vibration element may be a sonic element. The vibration element may be an ultrasonic element. The bio-stimulus transducer may include at least one thermal element. The thermal element may include a heating element. The thermal element may include a cooling element. The bio-stimulus transducer may include at least one mechanical element. The stimulator body may further include a central drainage lumen. At least the distal end of the device may include a flexible outer stimulator body.

In a further example, a device for stimulating the lacrimal system may include a stimulator body having a power source and a control subsystem with a distal end bio-stimulus transducer in electronic communication the control subsystem. The power source may include a battery and the control subsystem may include at least logic and communication circuits. Additionally the device may include a proximal end faceplate. The faceplate may include at least one sensor and at least one antenna in electronic communication with the control subsystem. In one example, the stimulator body may further include an isolation coupling between the control subsystem and the bio-stimulus transducer. In one example, the battery may be rechargeable. In one example, the isolation coupling may be a vibration-dampening element. In one example, the control subsystem may further include a memory to store operational data from the stimulator and may be configured to retrieve data from the antenna. In one example, the sensors may evaluate conductivity. The sensor may be a molecular sensor. The sensor may be a biological sensor. The antenna may be a communication antenna. The antenna may further include a radio frequency (RF) power amplifier. At least the distal end of the device may include a flexible outer stimulator body. The bio-stimulus transducer may further include multiple zones comprising electrodes. The stimulator body may further include at least one distal end magnetic component. The stimulator body may further include at least one distal end magnetic component that pairs with a second device. The second device may include another stimulator device. The bio-stimulus transducer may include at least one vibration element. The bio-stimulus transducer may include at least one thermal element. The thermal element may include a heating element. The thermal element may include a cooling element. The bio-stimulus transducer may include at least one mechanical element.

In a further example, a method for treating a condition of an eye of a subject may include providing a subject including a lacrimal system and a lacrimal system stimulation device. The device may include a stimulator body including a power source and a control subsystem with a distal end bio-stimulus transducer. The bio-stimulus transducer may be capable of inducing reflex tear activation within the subject, and may be in electronic communication with the control subsystem. The power source may include a battery and the control subsystem may include at least logic and communication circuits. The device may further include a proximal end faceplate including at least one sensor and at least one antenna in electronic communication with the control subsystem. The method may further include implanting the distal end of the device into a punctum of the lacrimal system such that the bio-stimulus transducer contacts the mucosal tissues of the lacrimal system and the proximal end faceplate contacts the punctum opening. The method also may include stimulating at least one site of the subject with the device so as to induce reflex tear activation. One site of the subject may include the mucosa of the lacrimal sac. One site of the subject may include the mucosa of the upper region of the nasolacrimal duct. One site of the subject may include the mucosa of the tear drainage system. The stimulating may include electrical stimulation. The stimulating may include mechanical stimulation. The stimulating may include chemical stimulation. The stimulating may include thermal stimulation. The expandable component may be expanded through a faceplate port by the injection of a substance to expand the expandable component(s) in the device. The expansion components may be used to enhance retention of the device in the tear drainage system and/or to enhance contact of the external surface of the device with surrounding mucosa. The stimulator body may include a helical outer wall. The helical outer wall may be configured to expand vertically. The helical outer wall may be configured as a horizontal anchor. The helical outer wall may enhance fixation of the device in the lumen of the punctum and canaliculi system. The helical outer wall may unwind once placed in the lumen of the punctum and canalicular system so that the helical outer wall may act as an anchor against the mucosa of the tear drainage system.

In a further example, a method for treating a condition of an eye of a subject may include stimulating at least one site of the subject, so as to treat the eye condition. The site may be selected from the group consisting of: at least one area of the mucosa of the upper region of the nasolacrimal duct of the subject, at least one area of the mucosa of the lacrimal sac of the subject, at least one area of the tear drainage system mucosa of the subject, and a conjunctiva and/or caruncle of the medial canthus of the subject. Stimulating the site may include stimulating to induce reflex tear activation, so as to treat the eye condition. The eye condition may include dry eye.

Further examples include devices, systems, and methods for treating one or more conditions (such as dry eye) by providing stimulation to the nasolacrimal system and/or the surrounding mucosa and adjacent structures. The devices and systems may be configured to stimulate the nasolacrimal system and/or the surrounding mucosa and adjacent structures. The devices may be implantable and may be disposable and/or biodegradable. The implant may reside in the nasolacrimal system (e.g., for example, punctum, canaliculi, nasolacrimal sac, nasolacrimal duct) and outside of the nasal cavity. The device may provide stimulus to the surrounding mucosa through vibrational energy (e.g., for example, sonic, ultrasonic, etc.) or through other stimuli such as high or low temperatures, mechanical stretch and relaxation or delivery of molecules that stimulate the surrounding mucosa and adjacent structures. The stimulus may induce a reflex arc through the nasociliary nerve to induce tearing from the lacrimal gland. The stimulus may be provided directly to the caruncle and/or conjuctiva of the medial canthus. The stimulus may be delivered on command through remote sensor communication. The stimulus may be programmed to deliver the stimulus on a specific pre-programmed schedule. The device may be removable via a minimally invasive procedure. The implant resides within the tear excretory pathway (punctum to nasolacrimal duct) which possess the capability to stimulate the mucosa of the lacrimal sac and upper region of the nasolacrimal duct (innervated by infratrochlear nerve a terminal branch of V1) and which leads to reflex tearing of the lacrimal gland which also innervated by V1. The stimulatory process may be through sonic, ultrasonic, mechanical, chemical, light or other means which may induce nerve response from the region of the lacrimal sac and nasolacrimal duct. The devices may include a stimulator body containing at least one bio-stimulus transducer or stimulator. The stimulus delivered by the stimulators described herein may be electrical, mechanical, thermal, chemical, light-based, magnetic, or the like. When the devices and systems are used to treat dry eye, the methods disclosed herein may include stimulating mucosa of the lacrimal sac and upper region of the lacrimal duct to increase tear production, reduce the symptoms of dry eye, and/or improve ocular health. The methods may further include treating dry eye by regular activation of the nasolacrimal reflex.

Further examples may include one or more devices for stimulating mucosa of the lacrimal sac and upper region of the nasolacrimal duct of a subject. The device may include a stimulator body and a bio-stimulus transducer connected to the stimulator body. The stimulator body may include a control subsystem to control a stimulus to be delivered to the subject via the bio-stimulus transducer. The bio-stimulus transducer may include at least the distal end of the device. The bio-stimulus transducer may include at least one electrode. The stimulus may be electrical. The electrode may include a hydrogel. The electrode may include one or more of platinum, copper, platinum-iridium, gold, or stainless steel. The stimulus may be a biphasic pulse waveform. The biphasic pulse waveform may be symmetrical. The frequency of the biphasic pulse waveform may be between about 20 Hz and about 80 Hz. The bio-stimulus transducer may be releasably connected to the stimulator body. The stimulator body may be reusable and the bio-stimulus transducer may be disposable. The device may include a user interface. The user interface may include one or more operating mechanisms to adjust one or more parameters of the stimulus. Additionally or alternatively, the user interface may include one or more feedback elements. The feedback elements may include haptic feedback elements.

The devices described herein may include systems for stimulating mucosa of the lacrimal sac and upper region of the nasolacrimal duct of a subject. The device may include a stimulator having a bio-stimulus transducer and a stimulator body including a power source and a control subsystem to control a stimulus to be delivered to the subject via the bio-stimulus transducer. The power source may include a battery. The power source may be rechargeable. The device may include a control subsystem. The control subsystem may include a battery, and logic and communication circuits. The device may include an isolation coupling. The battery may be rechargeable. The isolation coupling may be a vibration-dampening element. The stimulator may include memory to store data configured to retrieve data from the stimulator. The device may include a proximal faceplate. The faceplate may include sensors. The sensors may evaluate conductivity. The sensor may be a molecular sensor. The sensor may be a biological sensor. The faceplate may include an antenna. The antenna may be a communication antenna. The antenna may include a radio frequency (RF) power amplifier. The sensor may be electronically connected to the logic and communication circuits. The antenna may be electronically connected to the logic and communication circuits. The bio-stimulus transducer may be electronically connected to the logic and communication circuits. The stimulator body may include a central drainage lumen. At least the distal end of the device may include a flexible outer stimulator body. The stimulator body may include multiple zones comprising electrodes. The stimulator body may include at least one distal end magnetic component. The stimulator body may include at least one distal end magnetic component that pairs with a second device. The second device may include another stimulator device.

In a further example, a method of tear production in a subject may include implantation of a medical device into the lacrimal gland through at least one punctum of the subject. The medical device may include a stimulator body having a faceplate, a bio-stimulus transducer, a power source and a control subsystem to control a stimulus to be delivered to the subject via the bio-stimulus transducer. The method may include positioning the bio-stimulus transducer in contact with the lacrimal system mucosa of the subject, and delivering a stimulus via the bio-stimulus transducer to produce tears. The lacrimal system mucosa may include the mucosa of the lacrimal sac and upper region of the nasolacrimal duct. The method may include positioning a second bio-stimulus transducer in contact with the lacrimal system mucosa of the subject. The stimulus may be electrical. The stimulus may be delivered for a 1 second to 5 minute period, and the Schirmer score over the 5 minute period may be at least 3 mm greater than a basal Schirmer score of the patient. In some of these variations, the Schirmer score over the 5 minute period may be at least 5 mm greater than a basal Schirmer score of the patient. The stimulus may be a biphasic pulse waveform. The biphasic pulse waveform may be symmetrical. The stimulus may be pulsed. The method may include positioning a bio-stimulus transducer in contact with the lacrimal system mucosa of the subject and delivering a stimulus via the bio-stimulus transducer to produce tears on a second occasion. The stimulus may be mechanical. The stimulus may be chemical.

In further examples, a method of improving ocular health in a patient may include positioning a bio-stimulus transducer in a lacrimal system of the patient, and delivering stimulation to the mucosa of the lacrimal sac and upper region of the nasolacrimal duct of the patient via the bio-stimulus transducer at least once daily during a treatment period including at least 2 days to improve the ocular health of the patient, wherein improved ocular health may be measured by decreased dry eye symptoms. The bio-stimulus transducer may include at least one electrode, and the stimulation may be electrical. In one example, decreased dry eye symptoms may be measured by the Ocular Surface Disease Index, and the Ocular Surface Disease Index may decrease by at least 10% within the treatment period, wherein the treatment period may include 7 days. The Ocular Surface Disease Index may decreases by at least 20% within the treatment period. Decreased dry eye symptoms may be measured by the Ocular Surface Disease Index, and the Ocular Surface Disease Index may decrease by at least 40% within the treatment period, wherein the treatment period may include 90 days. The Ocular Surface Disease Index may decrease by at least 50% within the treatment period. The stimulation may activate the nasolacrimal reflex. The bio-stimulus transducer may be positioned in contact with lacrimal system mucosa of the patient. The bio-stimulus transducer may be positioned in contact with lacrimal system mucosa of the patient. The bio-stimulus transducer may include at least one electrode. The electrical stimulation may include a biphasic pulse waveform. The biphasic pulse waveform may be symmetrical. The frequency of the biphasic pulse waveform may be between about 20 Hz and about 80 Hz. The stimulation may be mechanical. The stimulation may be chemical. The stimulation may be thermal.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure. The drawings are only for the purpose of illustrating aspects of the disclosure and are not to be construed as limiting the disclosure.

Figure 1:
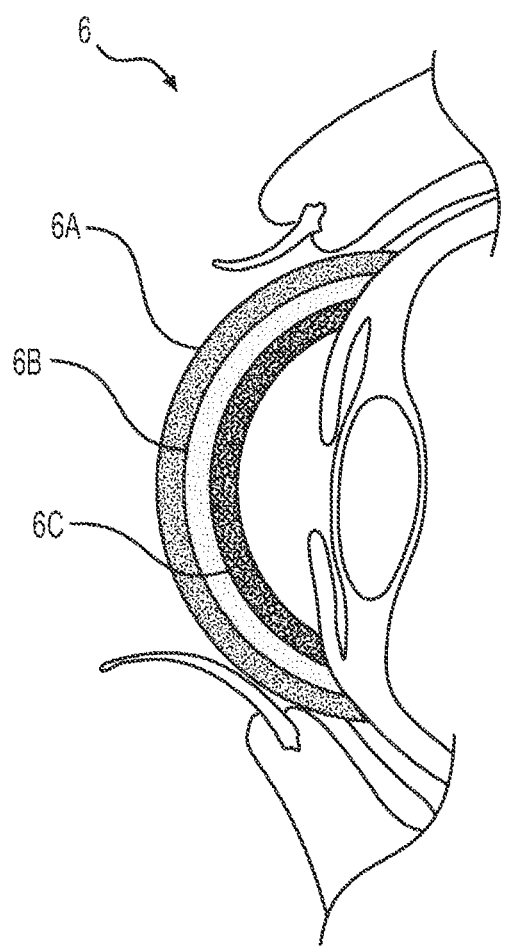
FIG. 1 illustrates a side-view of an eye of a subject, depicting the three layers of naturally produced tears.

It may be understood that both the foregoing general description and the following detailed description are exemplary and explanatory only and are not restriction of the disclosure.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

Definitions

To facilitate the understanding of this disclosure, a number of terms are defined below. Terms defined herein have meanings as commonly understood by a person of ordinary skill in the areas relevant to the present disclosure. Terms such as "a," "an," and "the" are not intended to refer to only a singular entity, but include the general class of which a specific example may be used for illustration. The terminology herein is used to describe specific examples of the disclosure, but their usage does not limit the disclosure.

As used herein, the term "patient" or "subject" refers to any living or non-living mammalian organism, such as a human, monkey, cow, sheep, goat, dog, cat, mouse, rat, guinea pig, and/or transgenic species thereof. In certain aspects, the patient or subject may be a primate. Non-limiting examples of human subjects are adults, juveniles, infants, and fetuses.

"Prevention" or "preventing" as used herein, includes, but is not limited to: (1) inhibiting the onset of a disease (e.g., DED) in a subject or patient which may be at risk and/or predisposed to the disease, wherein such inhibition may be either partial or complete, but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "ocular health" refers to restoring or maintaining a physiologically normal (e.g., healthy) amount, level, and/or degree of tears in the eye to minimize or alleviate dryness and related discomfort and to maintain eye health. Such minimization and/or alleviation of dryness may treat or prevent at least one symptom associated with DED such as, e.g., stinging, burning, and/or scratchy sensation in the eyes; stringy mucus in or around an eye; increased eye irritation from smoke or wind; eye fatigue; eye sensitivity to light; eye redness; a sensation of having something in your eyes; difficulty wearing contact lenses; periods of excessive tearing; and blurred vision, often worsening at the end of the day or after focusing for a prolonged period.

"Therapeutically effective amounts" and "pharmaceutically effective amounts," as used herein, indicate that amount which, when administered to a subject or patient for treating a disease, is sufficient to effect such treatment for the disease or to ameliorate one or more symptoms of the disease or condition (e.g., ameliorate pain).

As used herein, the terms "treat," "treating," and/or "treatment" are not limited to cases in which the subject (e.g., patient) is cured and the disease is eradicated. Rather, treatment also may merely reduce symptoms, improve (to some degree) a condition of the patient and/or subject, and/or delay disease progression, among other effects. It is not intended that treatment be limited to instances wherein a disease or affliction is cured. It is sufficient that symptoms are reduced.

As used herein, the terms "medical device," "implant," "device," "medical implant," "implant/device," and the like are used synonymously to refer to any object that is designed to be placed partially or wholly within a patient's body for one or more therapeutic or prophylactic purposes such as, e.g., for tissue augmentation, tissue stimulation, contouring, restoring physiological function, repairing and/or restoring tissues damaged by disease or trauma, and/or delivering therapeutic agents to normal, damaged, and/or diseased organs and tissues. While medical devices are often composed of biologically compatible synthetic materials (e.g., medical-grade stainless steel, nitinol, titanium, and/or other metals; exogenous polymers, such as polyurethane, silicone, PLA, PLGA, PGA, PCL, etc.), other materials also may be used in the construction of the medical implant. While not limiting the present disclosure to any particular device, specific medical devices and implants that are particularly relevant to this disclosure include stents, punctal plugs, Crawford tubes, catheters, lacrimal tubes, ocular or other shunts. In some examples, the device may incorporate a contrast material and/or opaque material(s) that may allow for visualization with standard imaging devices (for example, barium to allow for x-ray visualization).

As used herein, the term "proximal" refers to a location situated and/or positioned toward a point of origin (e.g., between a physician and a lacrimal implant device). In other words, the term "proximal" may refer to a position relatively closer to the exterior of the body of the patient or subject, and/or closer to an operator, physician, or medical professional.

As used herein, the term "distal" refers to a location situated and/or positioned away from a point of origin (e.g., behind a lacrimal implant device relative to a physician). In other words, the term "distal" may refer to a position relatively further away from the operator, physician, or medical professional, or closer to the interior of the body of the patient or subject.

As used herein, the term "implanted" refers to a state in which a device is completely or partially placed within a host. A device is partially implanted when some of the device reaches, or extends to the outside of, a host.

As used herein, the term "biomaterial" refers to any substance (other than drugs) or combination of substances synthetic or natural in origin, which can be used for any period of time, as a whole or as a part of a system which treats, augments, or replaces any tissue, organ, or function of the body.

As used herein, the term "biocompatibility" refers to the ability of a material to perform with an appropriate host response in a specific application.

Figure 2:
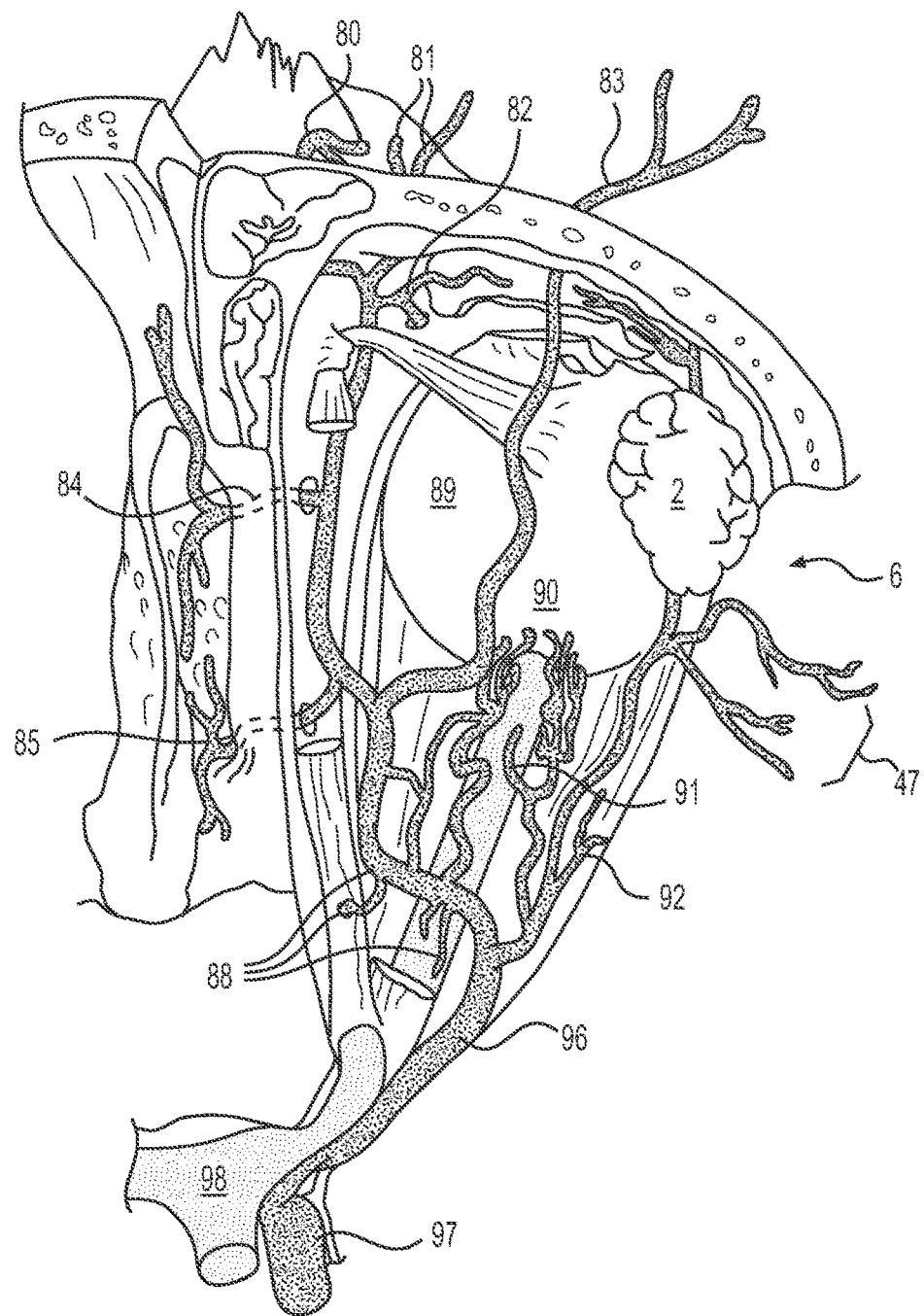
FIG. 2 illustrates anatomical features of nerves and blood vessels related to the eye and lacrimal system of a subject.

As used herein, the terms "tear drainage system," "nasolacrimal drainage system," and "lacrimal drainage system," refer to any connected anatomical structures having two small openings (e.g., for example, puncta). For example, a puncta may be located in an upper and/or lower eyelid, wherein these small openings lead into a small tube (e.g., for example, a canaliculus) which, in turn, empties into a lacrimal sac 16 and then into a canal called the nasolacrimal duct 18 (FIG. 2).

As used herein, the term "vibrating element" refers to a device part that changes electrical energy into mechanical or vibrational energy and transfers the vibrational energy, directly or indirectly, to a vibratable member. For example, piezoelectric substances are typically polarized crystalline materials which may transform electrical energy into mechanical energy. Piezoelectric materials also may emit vibrational waves in a variety of particular directions. Ceramic piezoelectric materials such as lead zirconium niobate are also useful.

As used herein, the term "sonic element" refers to a vibrating element device part which is capable of producing sound waves. Sonic devices generally operate between about 20 Hz and about 20 kHz.

As used herein, the term "ultrasonic element" refers to a vibrating element device part which is capable of producing ultrasonic sound waves. Ultrasound devices operate with frequencies from about 20 kHz to about several gigahertz.

DESCRIPTION

Overview

Dry Eye Syndrome

Dry eye is a condition in which there are insufficient tears to lubricate and nourish the eye. Tears are necessary for maintaining the health of the front surface (e.g., cornea, the ocular surface) of the eye and for providing clear vision. People with dry eyes either do not produce enough tears or have a poor quality of tears. Dry eye is a common and often chronic problem, particularly in older adults. Tsubota, K. (1998) "Tear Dynamics and Dry Eye," *Prog. Retin. Eye Res* 17(4), 565-596, describes the dry eye condition in greater detail and is incorporated by reference herein.

With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose. Dry eyes can result from an improper balance of tear production and drainage.

Inadequate Amount of Tears—

Tears are produced by several glands in and around the eyelids. Tear production tends to diminish with age, with various medical conditions, or as a side effect of certain medicines or procedures. Environmental conditions such as wind and dry climates can also affect tear volume by increasing tear evaporation. When the normal amount of tear production decreases or tears evaporate too quickly from the eyes, symptoms of dry eye can develop.

Poor Quality of Tears—

As discussed in further detail below, tears are made up of three layers: oil, water, and mucus. Each layer serves a function in protecting and nourishing the front surface of the eye. A smooth oil layer helps to prevent evaporation of the water layer, while the mucin layer functions in spreading the tears evenly over the surface of the eye. If the tears evaporate too quickly or do not spread evenly over the cornea due to deficiencies with any of the three tear layers, dry eye symptoms can develop.

The most common form of dry eyes is due to an inadequate amount of the water layer of tears. This condition, called keratoconjunctivitis sicca (KCS), is also referred to as dry eye syndrome.

People with dry eyes may experience symptoms of irritated, gritty, scratchy, or burning eyes, a feeling of something in their eyes, excess watering, and blurred vision. Advanced dry eyes may damage the front surface of the eye and impair vision.

Treatments for dry eyes aim to restore or maintain the normal amount of tears in the eye to minimize dryness and related discomfort and to maintain eye health.

What Causes Dry Eyes?

The majority of people over the age of 65 experience some symptoms of dry eyes. The development of dry eyes can have many causes. They include:

Age—

Dry eye is a part of the natural aging process. The majority of people over age 65 experience some symptoms of dry eyes.

Dehydration—

Lack of proper hydration may result in poor tear production.

Hormonal Deficiencies or Changes and Gender—

Thyroid conditions, hormonal changes during menopause, decreased production of androgen, estrogen supplementation (there are reports both of this improving dry eye conditions and worsening them), and women are more likely to develop dry eyes due to hormonal changes caused by pregnancy, the use of oral contraceptives, and menopause.

Medications—

Certain medicines, including antihistamines, decongestants, blood pressure medications, allergy medications, antidepressants, (e.g. amitriptyline, diazepam), parkinson's medications, birth control pills, diuretics, beta blockers, sleeping pills, many pain medications, and certain medications which regulate heart rhythm irregularities, can reduce the amount of tears produced in the eyes.

Medical Conditions—

Persons with rheumatoid arthritis, diabetes and thyroid problems are more likely to have symptoms of dry eyes. Also, problems with inflammation of the eyelids (blepharitis), inflammation of the surfaces of the eye, or the inward or outward turning of eyelids can cause dry eyes to develop. Corneal ulcers and infections, eye infections, such as conjunctivitis.

Other Conditions—

Vitamin A deficiency, secondary tearing deficiency (associated with disorders such as—lymphoma, leukemia, GVHD (graft vs. host disease, after a transplant), and rheumatoid arthritis), Parkinson's disease, Sjögren's syndrome (an auto-immune disease), Rheumatoid arthritis, Lupus, Lacrimal gland deficiency, Diabetes, Sarcoidosis, Stevens-Johnson syndrome, and Rosacea: Facial rosacea is commonly associated with ocular rosacea, which causes conditions such as blepharitis.

Environmental Conditions—

Exposure to smoke, wind, dry climates, high altitudes, excessive sun exposure, central heating, air conditioning, hair dryers, cigarette smoke, air pollution, and air travel can increase tear evaporation resulting in dry eye symptoms. Failure to blink regularly, such as when staring at a computer screen for long periods of time, can also contribute to drying of the eyes.

Low Blink Rate—

Blinking is critical in spreading tears over the surface of the eye and stimulating tear production. A chronic low blink rate is associated with dry eye symptoms. Computer use, reading, and watching TV are the three activities most commonly associated with a low blink rate.

Other Factors—

Long-term use of contact lenses can be a factor in the development of dry eyes. Refractive eye surgeries, such as LASIK, can cause decreased tear production and dry eyes. A temporary or permanent side effect of LASER vision correction surgery such as LASIK or photorefractive keratectomy (PRK).

How are Dry Eyes Diagnosed?

Dry eyes can be diagnosed through a comprehensive eye examination. Testing, with special emphasis on the evaluation of the quantity and quality of tears produced by the eyes, may include: Patient history to determine any symptoms the patient is experiencing and the presence of any general health problems, medications taken, or environmental factors that may be contributing to the dry eye problem. External examination of the eye, including lid structure and blink dynamics. Evaluation of the eyelids and cornea using bright light and magnification. Measurement of the quantity and quality of tears for any abnormalities. Special dyes may be instilled in the eyes to better observe tear flow and to highlight any changes to the outer surface of the eye caused by insufficient tears.

Schirmer's Test

Schirmer's test determines whether the eye produces enough tears to keep it moist. This test is used when a person experiences very dry eyes or excessive watering of the eyes. It poses no risk to the subject. A negative (more than 10 mm of moisture on the filter paper in 5 minutes) test result is normal. Both eyes normally secrete the same amount of tears.

Schirmer's test uses paper strips inserted into the eye for several minutes to measure the production of tears. The exact procedure may vary somewhat. Both eyes are tested at the same time. Most often, this test consists of placing a small strip of filter paper inside the lower eyelid (inferior fornix). The eyes are closed for 5 minutes. The paper is then removed and the amount of moisture is measured. Sometimes a topical anesthetic is placed into the eye before the filter paper to prevent tearing due to the irritation from the paper. The use of the anesthetic ensures that only basal tear secretion is being measured. This technique measures basic tear function.

A young person normally moistens 15 mm of each paper strip. Because hypolacrimation occurs with aging, 33% of normal elderly persons may wet only 10 mm in 5 minutes. Persons with Sjögren's syndrome moisten less than 5 mm in 5 minutes.

Alternatives to Schirmer's Test

Even though this test has been available for over a century, several clinical studies have shown that it does not properly identify a large group of patients with dry eyes. Newer and better tests of tear production and function are now emerging.

One test measures an iron-binding molecule called lactoferrin. The amount of this molecule appears to be closely related to tear production. Patients with low tear production and dry eyes have low levels of this molecule. This test may be especially valuable for patients with dry eyes since it can point to specific treatment strategies for dry eye.

The tears also may be examined for their content of lysozyme, an enzyme normally found in tears.

Another test involves fluorescein eye drops, which contain a dye that is placed in the eye. The dye should drain with the tears through the lacrimal duct into the nose within 2 minutes. If patients do not have enough tears to flush the dye into the nose, this time will be longer. A new test is also available to more accurately measure the flow of dye out of the eye.

Reflex Tearing

Reflex tearing is produced by strong physical or emotional stimulation of the lacrimal gland. The tears thus produced contain essential components, such as vitamin A and EGF, for the proliferation and differentiation of the corneal and conjunctival epithelium. Even if basic tearing is decreased, accelerating desiccation of the ocular surface, if reflex tears are present, they can provide the ocular surface epithelium with substances necessary for proper epithelial wound healing.

The Schirmer test without topical anesthesia, in which the test strip stimulates the cornea, conjunctiva and lid margin, has generally been used to measure reflex tearing. However, a result of 0 mm does not necessarily mean that the patient is incapable of producing reflex tears. Schirmer described the measurement of reflex tearing by stimulating the nasal mucosa with a camel's hair brush after anesthetizing the ocular surface with 4% cocaine. To check maximal reflex tearing, the Schirmer II test can be modified by using a cotton swab to stimulate the nasal mucosa without any anesthetic. Although the Schirmer II test is rarely used because either reflex tearing is assumed to be intact or the regular Schirmer test is considered more accurate, certain dry eye patients have been seen who are incapable of reflex tearing, and for whom the stimulate the nasal mucosa without any anesthetic is an important test.

How are Dry Eyes Treated?

One of the primary approaches used to manage and treat mild cases of dry eyes is adding tears using over-the-counter artificial tear solutions.

Dry eyes can be a chronic condition, but your optometrist can prescribe treatment to keep your eyes healthy, more comfortable, and prevent your vision from being affected.

The primary approaches used to manage and treat dry eyes include adding tears, conserving tears, increasing tear production, and treating the inflammation of the eyelids or eye surface that contributes to the dry eyes.

Adding Tears—

Mild cases of dry eyes can often be managed using over-the-counter artificial tear solutions. These can be used as often as needed to supplement natural tear production. Preservative-free artificial tear solutions are recommended because they contain fewer additives that could further irritate the eyes. However, some people may have persistent dry eyes that don't respond to artificial tears alone. Additional steps may need to be taken to treat their dry eyes.

Conserving Tears—

An additional approach to reducing the symptoms of dry eyes is to keep natural tears in the eyes longer. This can be done by blocking the tear ducts through which the tears normally drain. The tear ducts can be blocked with tiny silicone or gel-like plugs that can be removed, if needed. A surgical procedure to permanently close tear ducts can also be used. In either case, the goal is to keep the available tears in the eye longer to reduce problems related to dry eyes.

Increasing Tear Production—

An optometrist may recommend prescription eye drops that help to increase production of tears, as well as omega-3 fatty acid nutritional supplements.

Treatment of the Contributing Eyelid or Ocular Surface Inflammation—

Prescription eye drops or ointments, warm compresses and lid massage, or eyelid cleaners may be recommended to help decrease inflammation around the surface of the eyes.

Self Care

Steps to reduce symptoms of dry eyes include: Remembering to blink regularly when reading or staring at a computer screen for long periods of time. Increasing the level of humidity in the air at work and at home. Wearing sunglasses outdoors, particularly those with wrap around frame design, to reduce exposure to drying winds and sun. Using nutritional supplements containing essential fatty acids may help decrease dry eye symptoms in some people. Avoiding becoming dehydrated by drinking plenty of water (8 to 10 glasses) each day.

Tear Stimulation by Direct Inducement of Reflex Tearing

One example of the present disclosure relates to stimulation of innervated areas proximal to the lacrimal system. More specifically, the nerve ending of interest (a branch of the nasociliary) is the anterior ethmoidal nerve 84 (as described in further detail below) that supplies sensory innervation to the mucous membrane of the nasal cavity and the infratrochlear nerve. The nasociliary nerve is a branch of the ophthalmic 96 division of trigeminal nerve. It is intermediate in size as compared to the other two branches of the ophthalmic division; frontal nerve 81 (larger) and lacrimal nerve 92 (smaller)(FIG. 2, as discussed in further detail below). Although stimulation of the nerves of the nasal cavity has been found in the prior art (e.g., Tsubota, K. (1998) "Tear Dynamics and Dry Eye," Prog. Retin. Eye Res 17(4), 565-596; Ackermann, D. M. et al. "Nasal Stimulation Devices and Methods," WIPO PCT Patent Publication Number WO/2014/172693, Application PCT/US2014/034733, filed Apr. 18, 2014. (published Oct. 23, 2014); and Fujisawa, A. et al. (2002) "The Effect of Nasal Mucosal Stimulation on Schirmer Tests in Sjögren's Syndrome and Dry Eye Patients," in Lacrimal Gland, Tear Film, and Dry Eye Syndromes 3 (Sullivan, D., et al., Eds.), pp 1221-1226, Springer US, each of which being incorporated herein by reference in its entireties), stimulation of the lacrimal system mucosal tissues and nerves therein have not.

The nasociliary nerve enters the orbit through the lower part of the superior orbital fissure, between the two heads of the lateral rectus muscle. It then crosses above the optic nerve 98 (cranial nerve II), and runs forward along the upper margin of the medial rectus muscle. Finally, the nerve ends by dividing into the anterior ethmoidal nerve 84 and the infratrochlear nerve.

The nasociliary nerve gives off a number of branches, as described below: Communicating branch to the ciliary ganglion: This communicating branch is actually composed of sensory fibers that arise in the eyeball. They pass to the ciliary ganglion via the short ciliary nerves. Then they pass through the ciliary ganglion without interruption and join the nasociliary nerve via the communicating branch.

Long ciliary nerves: These are two or three small branches that arise from the nasociliary nerve while it crosses the optic nerve 98 in the orbital cavity. The long ciliary nerves pass forward alongside the short ciliary nerves and pierce the sclera of the eyeball. Then they continue forward between the sclera and the choroid to reach the iris. These nerves contain sympathetic fibers for the dilator pupillae muscle. Thus they have a role in the pupillary reflex (light reflex).

Posterior Ethmoidal Nerve 85:
This branch of the nasociliary nerve supplies the sphenoidal and ethmoidal air sinuses.

Infratrochlear Nerve:
This is a terminal branch of the nasociliary nerve that passes forward below the pulley (trochlea) of the superior oblique muscle and innervates the skin of the medial part of the upper eyelid. It also innervates the adjacent part of the nose.

Anterior Ethmoidal Nerve 84:
It is also a terminal branch of the nasociliary nerve. It passes through the anterior ethmoidal foramen to enter the anterior cranial fossa on the upper surface of the cribriform plate of ethmoid bone. The nerve then enters the nasal cavity through a slit like opening near the crista galli. It supplies the mucous membrane here. After supplying the mucous membrane, the anterior ethmoidal nerve 84 appears on the face at the lower border of the nasal bone as the external nasal branch. Here it supplies the skin of the nose as far down as the tip.

Nerve Supply of the Excretory System
Sensory nerve supply to the lacrimal sac 16 is derived from the infratrochlear nerve, which is the terminal branch of the nasociliary nerve, a branch of the ophthalmic division of the fifth cranial nerve ($V^1$). The lower portion of the nasolacrimal duct 18 receives sensation from the anterior superior alveolar branch of the maxillary division of the fifth cranial nerve ($V^2$).

There may be a physiologic relationship between the innervation of the lacrimal gland 2 (lacrimal nerve 92) and the lacrimal sac 16 (infratrochlear nerve), both being branches of the ophthalmic division of the fifth cranial nerve. This may explain why destruction of the lacrimal sac 16 leads to a decrease in tear secretion and why the epiphora of dacryocystitis may be caused in part by reflex irritation from the diseased sac 16 as well as from obstruction (see, e.g., Whitnall, S. E. (1932) in The Anatomy of the Human Orbit and Accessory Organs of Vision 2nd ed., pp 208-252, Oxford University Press, London; and Iwamoto, T. and Jakobiec, F. (1982) "Lacrimal Glands," in Biomedical Foundations of Ophthalmology, Harper & Row, Philadelphia, each of which is incorporated by reference herein in its entirety.)

The present disclosure involves an implant that resides within the tear excretory pathway (puncta 10 to nasolacrimal duct 18) which possess the capability to stimulate the mucosa of the lacrimal sac 16 and upper region of the nasolacrimal duct 18 (innervated by infratrochlear nerve a terminal branch of $V^1$) and which leads to reflex tearing of the lacrimal gland 2 which also innervated by $V^1$. The stimulatory process is through sonic, ultrasonic, mechanical, chemical, light or other means which might induce nerve response from the region of the lacrimal sac 16 and nasolacrimal duct 18. It should also be noted that the stimulatory force might extend past medial tissues to influence the septum of the nose which is also supplied by terminal branches of $V^1$ and which can also cause reflex tearing. More specifically, the nerve ending of interest (a branch of the nasociliary) is the anterior ethmoidal nerve 84 which supplies sensory innervation to the mucous membrane of the nasal cavity.

According to aspects of the current disclosure, an implanted medical device may be designed as a lacrimal system stimulator. It is a lacrimal system device with a bio-stimulus transducer and a faceplate and also may have an associated expandable component which may be implanted so that the distal end may be expanded to conform to anatomical features of the lacrimal system and the proximal end faceplate is proximate to the tear film abutting the upper or lower punctum 10.

In order to eye treat dry eye, drugs are often required to be administered to the eye. A conventional method of drug delivery is by topical drop application to the eye's surface. Topical eye drops, though effective, can be inefficient. As one example, when an eye drop is instilled in an eye, it often overfills the conjunctival sac (i.e., the pocket between the eye and the lids) causing a substantial portion of the drop to be lost due to overflow of the lid margin and spillage onto the cheek. In addition, a large portion of the drop remaining on the ocular surface can be washed away into and through a lacrimal canaliculus, thereby diluting the concentration of the drug before it can treat the eye. Moreover, topically applied drugs often have a peak ocular effect for about two hours post-application, after which additional applications of the drugs should be, but are often not, administered to maintain the desired drug therapeutic benefit.

To compound ocular management difficulty, patients often do not use their eye drops as prescribed. This poor compliance can be due to, for example, an initial stinging or burning sensation caused by the eye drop and experience by a patient. Instilling eye drops in one's own eye can be difficult, in part because of the normal reflex to protect the eye. Therefore, one or more drops may miss the eye. Older patients may have additional problems instilling drops due to arthritis, unsteadiness, and decreased vision. Pediatric and psychiatric populations pose difficulties as well.

Conditions of dry eye have been treated by blocking the tear flow from the eye into and through the lacrimal canaliculus 12. This has involved closing the canaliculus 12 by stitching the puncta 10 shut or by using electrical or laser cauterization to seal the puncta 10. Although such procedures can provide the desired result of blocking tear flow to treat a dry eye, they are unfortunately not reversible without reconstructive surgery.

In a field different from ocular management, control of respiration-related (e.g., allergies) diseases or disorders often requires repetitive manual digestion or other intake of a medication, and as such, can be ineffective due to a lack of patient compliance or non-localized drug delivery.

The Effect of Punctal Occlusion on Tear Production, Tear Clearance, and Ocular Surface Sensation in Normal Subjects Ocular irritation is a common complaint encountered by ophthalmologists. The mechanisms by which symptoms of irritation develop are still unclear; however, most patients with ocular irritation have been found to have a reduced tear break up time, indicative of tear film instability. This may be the result in part of an aqueous tear deficiency, a lipid tear deficiency from meibomian gland disease, or other undefined causes. Recently, delayed tear clearance of fluorescein has been shown to correlate strongly with the severity of ocular irritation symptoms independent of aqueous tear production. Corneal and conjunctival sensitivity to touch were both found to decrease as tear clearance worsened. Furthermore, the concentration of the proinflammatory cytokine interleukin-1a in tear fluid has been shown to increase with progressive delay of tear clearance. These findings suggest that delayed tear clearance may lead to chronic ocular surface inflammation that affects ocular surface tactile sensation and causes irritation symptoms. These findings suggest that treatment of ocular irritation should therefore be directed toward modulating the ocular surface environment.

Although the most commonly used therapy for ocular irritation is instillation of artificial tears, the improvement in symptoms is often short-lived, because the tears evaporate and drain through the lacrimal drainage system. Punctal occlusion is a simple procedure that can be used in an attempt to conserve naturally produced tears and also to prolong the contact time of artificial tears. The procedure has been shown to decrease elevated tear osmolarity and rose bengal staining of the ocular surface, consistent with increased tear volume from retention of aqueous tears. Punctal occlusion may have effects on tear physiology in addition to simple mechanical blockage of the lacrimal outflow tract. Decreased tear turnover after punctal occlusion, which could result from decreased drainage or reduced production of aqueous tears, has been previously reported (e.g., Yen, M. T. et al. (2001) "The Effect of Punctal Occlusion on Tear Production, Tear Clearance, and Ocular Surface Sensation in Normal Subjects," *Am. Ophthalmol.* 131/(3), 314-323, incorporated herein by reference in its entirety). Paradoxically, complete occlusion of the lacrimal drainage system often does not result in frank epiphora. These findings suggest that punctal occlusion may have an active, although still undefined, role in tear and ocular surface physiology. The purpose of the study was to evaluate the effect of temporary punctal occlusion on tear production, tear clearance, and ocular surface sensation in normal subjects.

Temporary punctual occlusions with silicone plugs is a simple procedure that can provide symptomatic relief to patients with ocular irritation symptoms, especially those with severe aqueous tear deficiency. It is generally believed that the therapeutic mechanism of punctal occlusion is to increase the aqueous component of the preocular tear film by blocking the lacrimal outflow tract. The study clearly shows that punctal occlusion also has profound effects on ocular surface sensation and aqueous tear production. Indeed, the results of the Yen study suggest that punctal occlusion influences the communication between the ocular surface and lacrimal gland 12.

The results of the Yen study also indicate that one likely mechanism by which punctal occlusion affects tear secretion is by reducing ocular surface sensation. We found that ocular surface sensation decreased after punctal occlusion. When only the lower puncta 10 were occluded, conjunctival sensation decreased significantly. However, no change in corneal sensation was noted in this group of subjects. One possible explanation for this finding may be that the Cochet-Bonnet anesthesiometer is not sensitive enough to measure subtle changes in corneal sensation. The cornea has a much greater sensory innervation compared with the conjunctiva. Because the anesthesiometer has a scale of only 0 to 6, it is plausible that any change in corneal sensation was not of sufficient magnitude to be measured with this instrument. Another possible explanation for the lack of any measurable change in corneal sensation could be that occlusion of a single punctum 10 of an eye is not adequate to produce a measurable decrease of corneal sensation. When both puncta 10 of one eye were occluded, conjunctival and corneal sensations were noted to decrease initially. In these normal subjects, however, the ocular surface sensation began to return to preocclusion levels by the end of the study. This finding suggests that an autoregulatory mechanism exists to normalize any changes in ocular surface sensation. This mechanism may be defective in patients with ocular irritation, because they have been noted to have decreased corneal sensitivity scores in multiple studies.

Consistent with the Yen findings of decreased ocular surface sensation is a concomitant decrease in sensory stimulated tear production, measured by the Schirmer 1 test, after punctal occlusion. In the subjects with both puncta 10 of one eye occluded, tear production began to stabilize toward the end of the observation period, similar to their ocular surface sensation. Several clinical reports have suggested that tear production and outflow of tears from the ocular surface are linked. Patients with acquired obstruction of the lacrimal drainage system rarely have symptoms of epiphora. Lack of significant epiphora has also been reported in patients with congenital absence of lacrimal puncta. Tomlinson and associates noted that a decrease in tear turnover correlated with a decrease in subjective symptoms of epiphora after punctal occlusion was performed. Aqueous tear production by the lacrimal 2 is mainly driven by sensory neural stimulation from the trigeminal nerves innervating the ocular surface, adnexa, and nasal mucosa. The Yen findings suggest that there may be receptors in the ocular surface, lacrimal outflow tract, or nasal mucosa that participate in a feedback mechanism controlling tear production. In contrast to the Yen findings in normal subjects, some dry eye patients have been reported to have increased Schirmer 1 test scores after punctal occlusion. Perhaps the underlying cause of aqueous tear deficiency in some dry eye patients is excessive negative feedback from the ocular surface or the tear drainage apparatus on lacrimal gland tear secretion. In these patients, punctal occlusion may reverse this process.

An interesting finding in the Yen study was that a decrease in tear production and ocular surface sensation was also measured in the contralateral nonoccluded eye. Decreased tear production in the contralateral eye has been reported in patients with unilateral neurotrophic keratitis. Crossed sensory stimulation of tear production has been postulated, with decreased trigeminal stimulation of one eye decreasing sensory stimulated tear production bilaterally. Another possibility is that a central control of tear production exists. A third possibility is that decreased ocular surface sensation results in a decreased blink rate, which promotes an increase in tear film evaporation. It would seem unusual for unilateral punctal occlusion to affect the ocular surface sensation in the contralateral eye. The same patients with unilateral neurotrophic keratitis were reported to have near-normal corneal sensation scores in the unaffected eye. Perhaps the decreased aqueous tear production in the contralateral eye that was observed after punctal occlusion leads to this decreased sensation. This is consistent with a correlation between tear production and ocular surface sensation that was previously observed in patients with aqueous tear deficiency. Another possibility is that decreased tear clearance leads to accumulation of such factors as opioid peptides or inflammatory cytokines in the tear film that affect the threshold of the sensory nerves on the ocular surface. Yet another possibility may be that changes in tear osmolality could act on the sensory nerves of the ocular surface to decrease sensation. Similar to the occluded eye, ocular surface sensation and tear production returned toward preocclusion levels over time in the fellow eye. Again this suggests that regulation of tear production is a dynamic process and that autoregulatory processes appear to exist that function to maintain tear homeostasis.

One implication of the Yen study may be that punctal occlusion may not be appropriate therapy for all patients with ocular irritation. Patients complaining of ocular irritation are often given a generic diagnosis of "dry eye." However, ocular irritation may have other underlying causes, such as meibomian gland dysfunction. The concentration of the proinflammatory cytokine interleukin-1a has also been found to increase in the tear fluid as tear clearance decreases. Ocular irritation may be caused by chronic ocular surface inflammation in some cases, and punctal occlusion in these patients may worsen their symptoms by further delaying their tear clearance and increasing the concentrations of pathogenic factors in the tear fluid. Anti-inflammatory therapy may be a better option for these patients. It is important to note that occlusion of only the inferior puncta in normal subjects did not significantly change their tear clearance. Therefore, additional studies will be required to assess the effects of therapeutic punctal occlusion in patients with dry eye disease. As greater knowledge is gained about the regulation of the ocular surface/lacrimal gland integrated unit, new paradigms may emerge regarding which patients with dry eye disease may benefit from punctal occlusion and which patients may have adverse consequences.

Tear production from the lacrimal gland appears to be tied to a stimulus in the tear drainage system. If a plug to close off the tear drainage system is implanted, the mucosa there is no longer stimulated and there is a reflex arc that may signal, trigger, or otherwise cause the lacrimal gland 2 to stop producing tears. This may mean that stimulating the mucosa, such as with the devices described herein, may induce the mucosa to signal that tears were coming in and may lead to more tear production.

DETAILED DESCRIPTION OF DRAWINGS

Described herein are devices, systems, and methods for treating one or more conditions (such as DED) by providing stimulation to mucosa of the lacrimal sac 16 and upper region of the nasolacrimal duct 18. In one example, the device is implantable. Additional, more than one device may be implantable per eye. In one example, two devices are implantable, one each through each punctum of an eye. In one example, two devices may be magnetically linked after implantation. Further, the devices may include a stimulator body and a bio-stimulus transducer, where the bio-stimulus transducer includes one or more stimulus delivery zones. The stimulus delivered by the stimulators described herein may in some variations be electrical; in other variations, they may be mechanical, thermal, chemical, light-based, magnetic, or the like. When the devices and systems are used to treat DED, the methods may include stimulating mucosa of the lacrimal sac 16 and upper region of the nasolacrimal duct 18 to increase tear production, reduce the symptoms of DED, or improve ocular health.

In one example, the present disclosure includes an implant (e.g., medical device, stimulator body) that resides in (e.g., is positioned within) the nasolacrimal system (puncta 10, canaliculi 12, lacrimal sac 16) and outside of the nasal cavity. The device provides stimulus to the surrounding mucosa through vibrational energy (sonic, ultrasonic) or through other stimuli such as high or low temperatures, mechanical stretch and relaxation, and/or delivery of molecules that stimulate the surrounding mucosa and adjacent structures. The stimulus then induces a reflex arc through the nasociliary nerve to induce tearing from the lacrimal gland 2. The stimulus may be delivered on command through remote sensor communication or programmed to deliver the stimulus on a specific pre-programmed schedule. The device is removable in minimally invasive fashion. In another example, the stimulus is provided directly to the caruncle 13 of the medial canthus. In one arrangement, the device contains sensors that communicate with both internal and external (remote) interfaces and send/receive data. Further, the device could be for short-term (hours to days) to long-term use (months to years). In one example, the device may be biodegradable or made from medical grade polymers and/or alloys that are not biodegradable (e.g., silicone, acrylics, hydrogels, NiTi, titanium, steel, gold, etc.).

FIG. 1 illustrates a side-view of an eye 6 of a subject, including three layers of naturally produced tears. For example, as shown in FIG. 1, naturally-produced tears are composed of an outer oily layer 6A, a middle watery layer (e.g., the aqueous layer) 6B, and an inner mucus layer 6C which spread across the surface of the eye 6 (e.g., the ocular surface) whenever the subject blinks, thereby providing lubrication, washing away foreign matter, reducing the risk of infection, and keeping the surface of the eye 6 smooth and clear.

FIG. 2 illustrates anatomical features of nerves and blood vessels related to eye 6 and the lacrimal system of a subject. Such nerves and blood vessels include the dorsal nasal vessel 80, the frontal 81, the medial palpebral 82, the supraorbital 83, the anterior ethmoidal 84, the posterior ethmoidal 85, the muscular 88, the bulb of the eye 89, the ciliary 90, the arteria centralis retinae 91, the lacrimal 92, the zygomatic branches 94, the ophthalmic 96, the internal carotid 97, the lacrimal gland 2, and the optic nerve 98.

Figure 3:
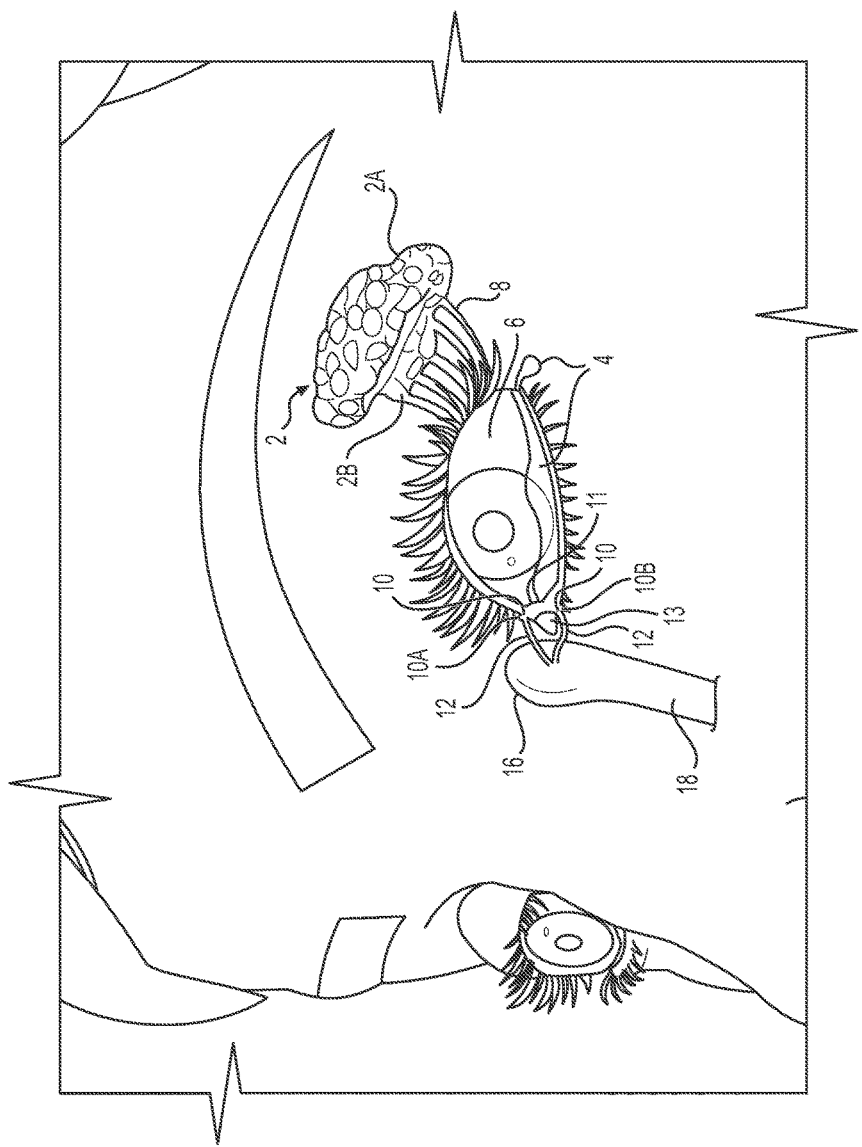
FIG. 3 illustrates anatomical features related to the eye and lacrimal system of a subject.

FIG. 3 illustrates additional anatomical features related to the lacrimal system of the eye 6 of a subject. As shown, the lacrimal gland 2 is positioned in the upper outer portion of the orbit of each eye 6. The lacrimal gland 2 includes the orbital (e.g., superior) portion 2A and the palpebral (e.g., inferior) portion 2B. The lacrimal gland 2 secretes the aqueous layer 6B of tears 4 which are delivered from the lacrimal gland 2 to the surface of the eye 6 via one or more channels or ducts 8 of the lacrimal gland 2. Tears 4 drain from the eye 6, towards a plica semilunaris 11 and lacrimal caruncle 13 via the nasolacrimal drainage system, which includes two puncta 10 located on a lacrimal papilla (e.g., superior lacrimal papilla 10A or inferior lacrimal papilla 10B). Each puncta 10 includes a minute orifice or opening in fluid communication with canaliculi 12. The canaliculi 12 converge and drain into the lacrimal sac 16, which in turn, is in fluid communication with the nasolacrimal duct 18.

Figure 4:
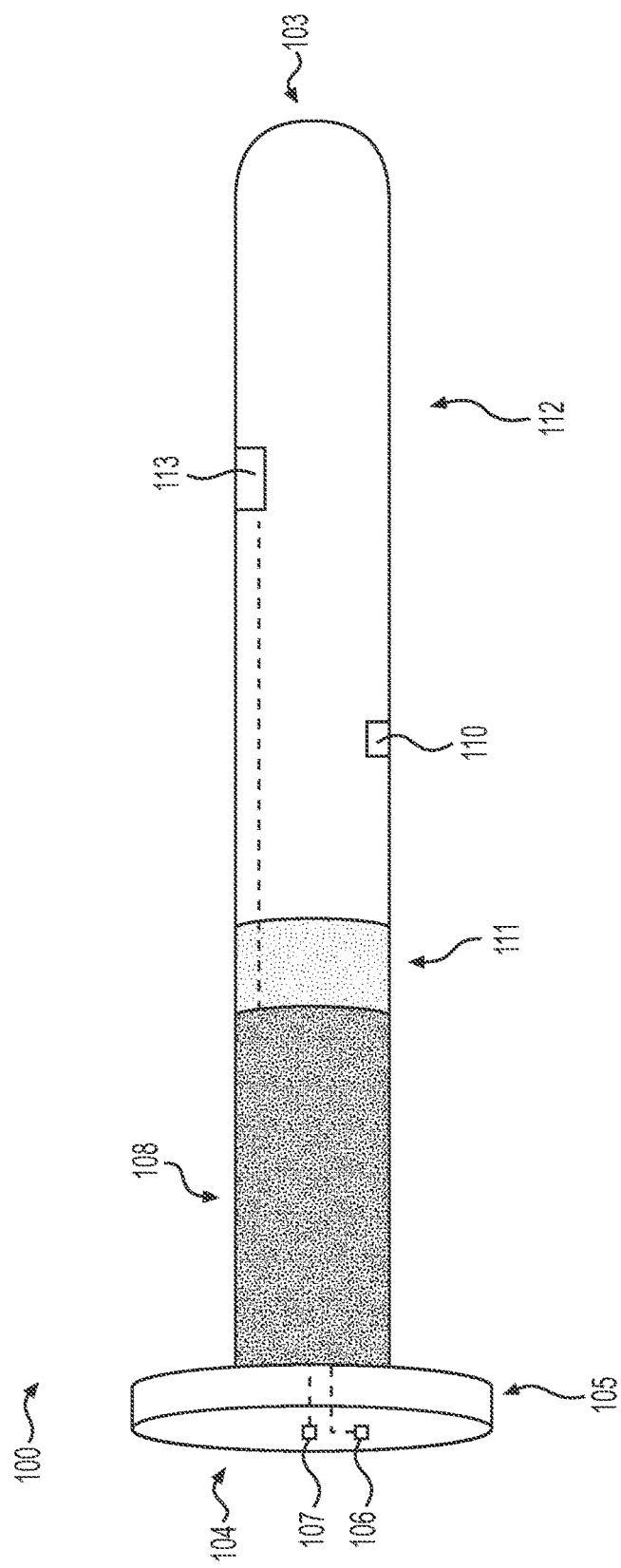
FIGS. 4 and 5 illustrate exemplary stimulators according to aspects of the current disclosure.

In order to induce tear production, one or more devices may be positioned within the nasolacrimal drainage system to prompt or stimulate the lacrimal gland 2. For example, FIG. 4 illustrates an exemplary medical device 100, e.g., stimulating device, according to aspects of the present disclosure. The device 100 may include a stimulator body 112 extending between a proximal end 104 and a distal end 103 and may have a length between about 1 mm and about 30 mm. In some arrangements, for example, stimulator body 112 have a length between about 25 mm and about 30 mm such that stimulator body 112 may extend through the puncta 10, through the canaliculus 12, and into the lacrimal sac 16 and/or the nasolacrimal duct 18. In other arrangements, however, stimulator body 112 may have a length between about 1 mm and about 10 mm. A diameter of stimulator body 112 may be between about 250 μm and about 1.5 mm. Stimulator body 112 may be tapered (e.g., comprise a varied diameter or dimension along its length) so as to narrow in the direction extending from proximal end 104 to distal end 103. In some exemplary arrangements, a distal-most end of stimulator body 112 may be about 500 μm to facilitate implantation, as will be described in further detail below.

The device 100 may include a power source 110 and a control subsystem 108 with a distal end bio-stimulus transducer 113 in electronic communication the control subsystem 108. In some aspects, the power source 110 may include a battery, and the control subsystem 108 may include at least logic and communication circuits. An enlarged faceplate 105 may be located at the proximal end 104 of the device 100 and may include at least one sensor 106 and at least one antenna 107 in electronic communication with the control subsystem 108. The simulator body 112 and the faceplate 105 may be formed (e.g., extruded, molded, etc.) as a one-piece continuous structure. Alternatively, in some arrangements, the stimulator body 112 may be joined to the faceplate 105 via any appropriate manner such as, for example, adhesive(s), mechanical faster(s), or welding. In one example, the device 100 may further include an isolation coupling 111.

Figure 5:
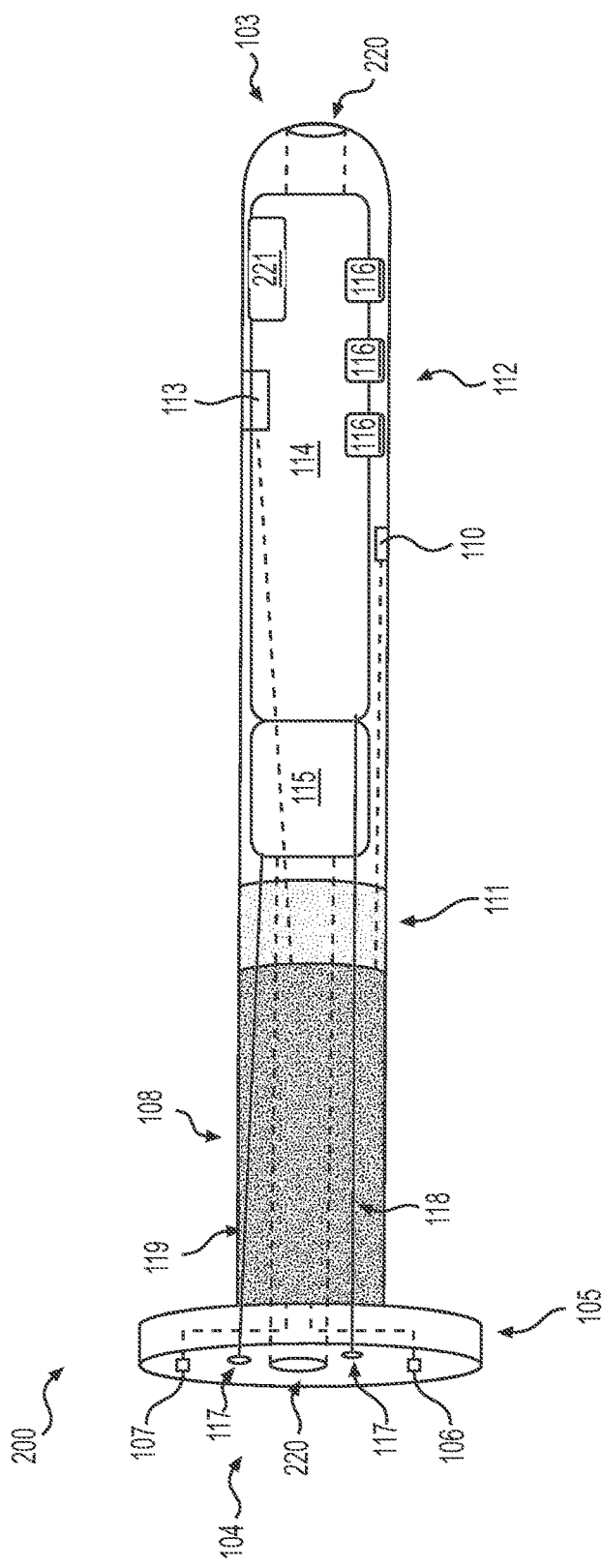

FIG. 5 illustrates an additional exemplary medical device 200, e.g., stimulating device, according to aspects of the present disclosure. Similar to device 100, the device 200 may include a stimulator body 112 comprising a power source 110 and a control subsystem 108 with a distal end bio-stimulus transducer 113 in electronic communication the control subsystem 108. The power source 110 may include a battery and the control subsystem 108 may include at least logic and communication circuits. Similar to device 100, device 200 may include a proximal end 104 faceplate 105. The faceplate 105 may include at least one sensor 106 and at least one antenna 107 in electronic communication with the control subsystem 108. In one example, the device 200 further includes an isolation coupling 111. The stimulator body 112 may further include a central drainage lumen 220. In one aspect, at least the distal end 103 of the device 200 may flexible. Additionally, the stimulator body 112 may further include an expandable component 114. The expandable component 114 may be connected to a faceplate port 117 via a lumen 118. Additionally, in some arrangements, the stimulator body 200 may further include a therapeutic agent reservoir 115 which may be connected to a faceplate port 117 via a lumen 119. In some aspects, the stimulator body 112 may further include multiple zones comprising electrodes 116. In one arrangement, the stimulator body 112 further includes at least one distal end magnetic component 221.

Figure 6:
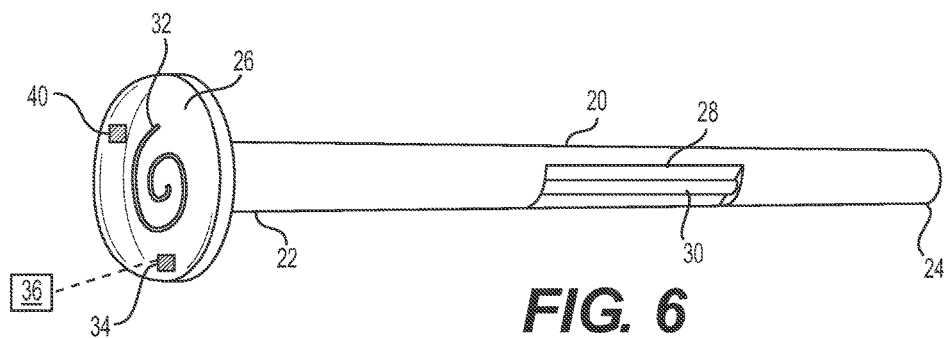
FIGS. 6-9 illustrate further exemplary stimulators according to aspects of the current disclosure.

FIGS. 6-9 illustrate further exemplary stimulators according to aspects of the current disclosure. For example, as shown in FIG. 6, an exemplary stimulator device may include a body 20 extending between a proximal end 22 and a distal end 24. The body 20 may have a length between about 1 mm and about 30 mm. In some arrangements, for example, the body 20 may have a length between about 25 mm and about 30 mm such that the body 20 may extend through the puncta 10, through the canaliculus 12, and into the lacrimal sac 16 and/or the nasolacrimal duct 18. In other arrangements, however, the body 20 may have a length between about 1 mm and about 10 mm. A diameter of the body 20 may be between about 250 μm and about 1.5 mm. As shown, the body 20 may be tapered (e.g., comprise a varied diameter or dimension along its length) so as to narrow in the direction extending from the proximal end 22 to the distal end 24. In some exemplary arrangements, a distal-most end of the body 20 may be about 500 μm to facilitate implantation, as will be described in further detail below.

The proximal end 22 may be coupled to or monolithically formed with a faceplate 26. For example, in some arrangements, the body 20 and the faceplate 26 may be formed (e.g., extruded, molded, etc.) as a one-piece continuous structure. Alternatively, in some arrangements, the body 20 may be joined to the faceplate 26 via any appropriate manner such as, for example, adhesive(s), mechanical faster(s), or welding. As shown in FIG. 6, the faceplate 26 may be enlarged relative to body 20. That is, a radial dimension (e.g., diameter) of the faceplate 26 may be larger than a radial dimension (e.g., diameter) of the body 20. In such a manner, the faceplate 26 may include a flange, collar, and/or projection which may be received adjacent (e.g., abutting) the puncta 10 of the nasolacrimal drainage system, as will be described in further detail below. Thus, the faceplate 26 also may function to plug or otherwise block a portion of the puncta 10 to prevent drainage of tears through puncta the 10. In some arrangements, the faceplate 26 may be rounded, curved, or non-planar, as shown in FIG. 6. As such, the entirety of the stimulator device may be atraumatic. The faceplate 26 may optionally include a coating or be impregnated with a photo-active material (not shown). Such photo-active materials may include, e.g., fluorescein which may be activated (e.g., excited) upon the application of an appropriate energy source such as, e.g., sunlight and/or ultraviolet light of a specific wavelength (e.g., blue light). Upon activation, the photo-active material may emit light within the visible spectrum. As such, a user may verify the proper placement of the faceplate 26 in or adjacent to the puncta 10 by observing the light emitted by the photo-active material.

The body 20 and the faceplate 26 may include any one or more biologically compatible materials such as, for example, medical-grade stainless steel, nitinol, titanium, etc.; and/or polymers, such as polyurethane, silicone, Polylactic acid (PLA), Polylactic-co-glycolic acid (PLGA), Polyglycolide (PGA), and/or Polycaprolactone (PCL). In some arrangements, an antimicrobial or other therapeutic agent (not shown) can be coated on, or impregnated in, at least a portion of the outer surface of the body 20 and/or the faceplate 26 to, e.g., prevent microbial growth. Optionally, the body 20 and/or the faceplate 26 may be micropatterned (e.g., manufactured) with grooves, recesses, or other surface irregularities (not shown). Such grooves may have a depth of between about 1 μm and about 50 μm and may decrease the overall surface area in contact with surrounding tissues. Such grooves also may prevent bacterial adherence to an outer surface of the body 20 and/or the faceplate 26.

Additionally or alternatively, a coating of Titanium Dioxide, Silver, or other such bacteriostatic or bactericidal materials may be applied to or impregnated within body 20 and/or faceplate 26. As shown in FIG. 6, the body 20 may include one or more cut-outs, openings, or windows 28. For example, the body 20 may include a single window 28, as shown in FIG. 6. Alternatively, however, the body 20 may include a pair of windows 28 on opposing sides of the body 20. That is, the windows 28 may be diametrically opposed and equidistantly spaced about a circumference of the body 20. The windows 28 also may be laterally, vertically, and/or radially offset from one another. In other arrangements, the body 20 may include any number of windows 28 positioned about the circumference of body 20. For example, the body 20 may include between about 1 and about 10 windows 28. The windows 28 may be equally spaced about a circumference of the body 20. Alternatively, the windows 28 may be unequally spaced about the circumference of the body 20. Each window 28 may be located at a common axial position between the proximal end 22 and the distal end 24 of the body 20. Alternatively, the windows 28 may be located at varying axial locations between the proximal end 22 and the distal end 24 of the body 20. For example, the body 20 may define a first "ring" or grouping of windows 28 arranged about the circumference of the body 20 at a first axial location and a second, or more "rings" or groupings of windows 28 arranged about the circumference of the body 20 at a second or more axial locations of the body 20.

As shown in FIG. 6, the window 28 may be rectangular. However, the window 28 may be square, circular, oval, triangular, polygonal, or irregular shaped without departing from the scope of this disclosure. Additionally, one or more windows 28 may have a different size and/or shape relative to another window 28. For example, each window 28 may have a varied size, shape, and/or orientation relative to any other window 28. The window 28 may include an opening in the body 20 so as to expose one or more stimulus delivery mechanisms such as, for example, a conductor 30. For example, the conductor 30 may include a conductive wire (e.g., a 30-guage wire). The conductor 30 also may include any suitable electrode (e.g., plate electrode). The conductor 30 may be, for example, comprised at least in part of one or more of copper, silver, aluminum, other such metals. Depending on the particular material selected, impedance of the conductor(s) 30 may be between about 800Ω and about 2,000Ω. For example, impedance of the conductor(s) 30 may be about 1,500Ω.

A pair of conductors 30 (only one visible in FIG. 6) may extend from the face plate 26 towards the distal end 24 of the body 20. In use, portions of the conductors 30 within the windows 28 may directly contact or touch tissue within the canaliculi 12. That is, the window(s) 28 is designed to expose the conductor(s) 30 to adjacent tissue (e.g., nerves, mucosa, etc.) for excitation or stimulation of such tissue. In some arrangements, a pair of conductors 30 may be arranged in a bipolar fashion. That is, a first conductor 30 may be configured as a first pole (e.g., anode) of a bipolar arrangement while a second conductor 30 may be configured as a second pole (e.g., cathode) of a bipolar arrangement. Alternatively, each conductor 30 itself may comprise a bipolar conductor. In such an arrangement, a return path (not shown) may be arranged along body 20 in the form of a reference electrode. Further, in some arrangements, the conductor(s) 30 may be arranged for single-channel or multi-channel stimulation of tissue. In such arrangements, constant current may be applied so that impedance at the load is not changing the amount of current that is reaching the tissue of interest during stimulation.

The faceplate 26 may include an inductive coil 32. The coil 32 may be operably coupled to the conductor(s) 30 and may wirelessly communicate with an external stimulation device. In some arrangements, the coil 32 may be a radiofrequency (RF) coil which may be configured to receive and/or transmit RF signals. For example, the coil 32 may be configured to facilitate communication of data and/or energy between the conductor(s) 30 and an external source. For example, in some arrangements, the coil 32 may be a portion of a control subsystem 34 which may optionally include a memory (not shown). The control subsystem 34 may be positioned on or within the faceplate 26. Alternatively, however, the control subsystem 34 may be positioned along or within body 20. The control subsystem 34 may be configured to communicate wirelessly (e.g., via Wi-Fi, Bluetooth, or the like) with an external device 36 (e.g., an external programmer, base station, laptop, computer, mobile device, phone, tablet, wearable computer (e.g., optical head-mounted displays such as Google Glass™) or the like). The external device 36 may inductively transfer energy to the coil 32. In some arrangements, the control subsystem 34 may be solely passive. That is, the control subsystem 34 may not be configured for active control of the stimulator device, but rather, only to execute commands received from the external device 36 or the like. Optionally, the control subsystem 34 may include a power source (e.g., battery) to supply power to the control subsystem 34. In some arrangements, the external device 36 may be positioned near or adjacent the implanted stimulator device including the coil 32, and a user may actuate the external device 36 to inductively deliver energy to the coil 32, and consequently, the conductor(s) 30.

The external device 36 may be used by the user (e.g., the subject themselves or a medical professional) to power the stimulator device on or off, start or stop stimulus, change an intensity of stimulus, change a duration of stimulus, change a stimulus pattern, or the like. In one arrangement, the external device 36 may be able to activate or deactivate different functions, and/or may be able to change different parameters, based on their manner of operation (e.g., pressing a button briefly, pressing a button for a prolonged period of time, pressing a button with a particular pattern of pressing actions, rotating a dial by different angles or different speeds). Each of the one or more operating mechanisms may be any suitable structure, such as but not limited to a button, slider, lever, touch pad, knob, or deformable/squeezable portion of the housing, and a stimulator may include any combination of different operating mechanisms.

Additionally or alternatively, in some variations external device 36 may include a display, which may be configured to convey information to a user via text and/or images. Additionally or alternatively, the external device 36 may include a speaker or buzzer configured to produce one or more speech prompts or other sounds. Additionally or alternatively, the external device 36 may be configured to vibrate. When external device 36 is configured to vibrate, the duration and/or repetition of the vibration may convey information to the user.

Optionally, the stimulator device may further include one or more sensors 40. As shown in FIG. 6, the sensor 40 may be positioned on the faceplate 26. However, the sensor 40 may be positioned along the body 20 without departing from the scope of this disclosure. The sensor 40 may be configured for sensing biochemical properties of tears 4 in the eye 6, placement of, and/or operation of the stimulator device. For example, the sensor 40 may sense a degree of conductivity, may be a molecular sensor, and/or may be a biological sensor. For instance, in some arrangements, the sensor 40 may evaluate or sense the degree of moisture adjacent the sensor 40, thereby evaluating whether additional tears 4 should be induced via application of stimulation by the conductor(s) 30. In some arrangements, the sensor 40 may communicate with the external device 36 (and/or an additional external device). In such arrangements, the proximity of the sensor 40, and therefore, the faceplate 26 or the body 20 relative to the external device 36, may be readily ascertained by a user to verify the proper placement of the faceplate 26 and/or the body 20 within the puncta 10 or the canaliculus 12.

Upon delivery of a signal from the external device 36, upon detecting a pre-determined condition via the sensor 40 (e.g., an indication of insufficient tears), or upon the expiration of a pre-determined period of time, energy may be delivered to tissue via the electrode(s) 30. For example, energy having a pulse rate of between about 1 Hz and about 200 Hz, with a pulse duration of between about 10 μsec to about 500 μsec, and having a pulse amplitude between about 0.1 mA to about 5 mA may be applied via electrode(s) 30. In some exemplary arrangements, energy may be delivered in the form of an active bi-phasic, symmetric, charged balance waveform with an interpulse delay of 100 μsec. A total treatment time may be between about 5 seconds and about 20 seconds.

In use, the stimulator device may be positioned inside the nasolacrimal drainage system through the puncta 10 and into a canaliculus 12. In all arrangements disclosed herein, however, the stimulator device is positioned externally of the nasal cavity. That is, while portions of the stimulator device may be received within the lacrimal sac 16 and the nasolacrimal duct 18, no portion of the disclosed stimulator devices is received at any time within the nasal cavity of a subject during use. In order to induce tears 4, the conductor(s) 30 may be energized to provide stimulus to the surrounding tissue in the canaliculus 12 through one or more of electrical excitement of tissue, a piezoelectric element for vibrational excitement (e.g., sonic or ultrasonic), and/or a heating/cooling element for thermal excitement. Further examples of stimulus may include one or more of a light-generating devices (not shown), magnetic-field generating devices (not shown), pulsed fluid (e.g., air) delivery devices (not shown), and/or chemical agents (not shown). The stimulus then induces a reflex arc through the tissue of the canaliculus 12. For example, the stimulus applied via the conductor(s) 30 may excite one or more of the nasociliary nerve, the supratrochlear nerve, and the infratrochlear nerve to induce tearing from the lacrimal gland 2. In one arrangement, the stimulator device could be arranged for short term (hours to days) or long term use (months to years). In some arrangements, the stimulator device may be biodegradable or made from medical grade polymers and/or alloys that are not biodegradable (silicone, acrylics, hydrogels, NiTi, titanium, steel, gold, etc.).

Figure 7:
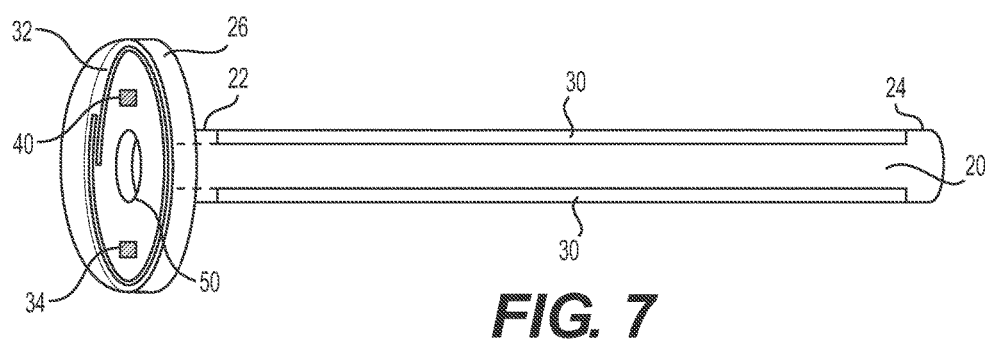
Figure 8:
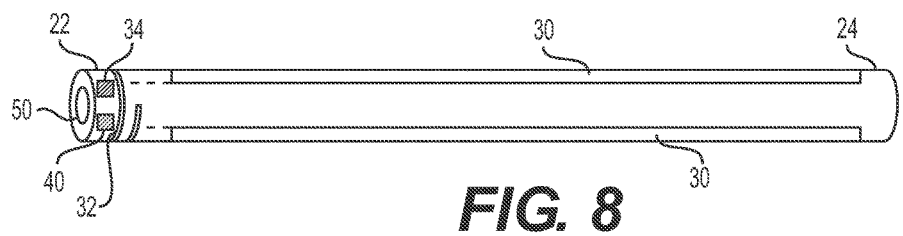

FIG. 7 illustrates a further exemplary arrangement of a stimulator device for stimulation of tissue. The stimulator device of FIG. 7 may be similar to that of FIG. 6, and as such, may include a pair of conductors 30 operably coupled to a coil 32 positioned in the faceplate 26. As shown in FIG. 7, the conductors 30 may extend along radially outer surfaces of the body 20. While not shown in FIG. 7, one or more windows similar to the window 28 shown in FIG. 6 may be arranged or embedded along portions of the body 20 so as to expose the conductors 30 to tissue. In other arrangements, the conductors 30 may extend along an exterior circumferential surface of body 20 and may be flush with an exterior surface of the body 20. In one arrangement, the conductors 30 may be embedded within the thickness of body 20. In addition, the stimulator device of FIG. 7 may include a lumen 50 extending through faceplate 26 and body 20. The lumen 50 may be configured to drain tears 4 therethrough from the proximal end 22 towards the distal end 24. In yet a further arrangement, as shown in FIG. 8, the faceplate 26 may be omitted. Instead, the coil 32 may be positioned on, embedded within, or arranged about the body 20. In addition, the control subsystem 34 and any sensors 40 may be positioned on or embedded within the body 20. In such arrangements, the entirety of the body 20 may be received within a canaliculus 12 of the nasolacrimal drainage system.

Figure 9:
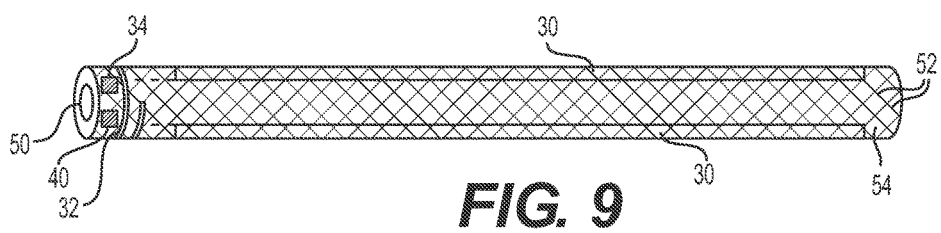

In a further arrangement, as shown in FIG. 9, the body 20 may be comprised of a braid or mesh 52. The mesh 52 may comprise a network of struts 52a forming a plurality of closed cells 54. Although not shown, in some arrangements, the porosity of the mesh 52 may vary along the length of the mesh 52. Optionally, the mesh 52 may be configured to expand to varying dimensions (e.g., diameters) along the length of the body 20. That is, portions of the mesh 52 may expand to a greater extent than other portions of the mesh 52 so as to form a series of peaks and valleys along the body 20. As such, the portions of the mesh 52 expanding to a greater extent (not shown) may firmly contact tissue, while the portions of the mesh 52 expanding to a lesser extent (not shown) may not be in contact with the tissue. As such, an overall pressure exerted by the body 20 on the tissue may be reduced or minimized.

Figure 10:
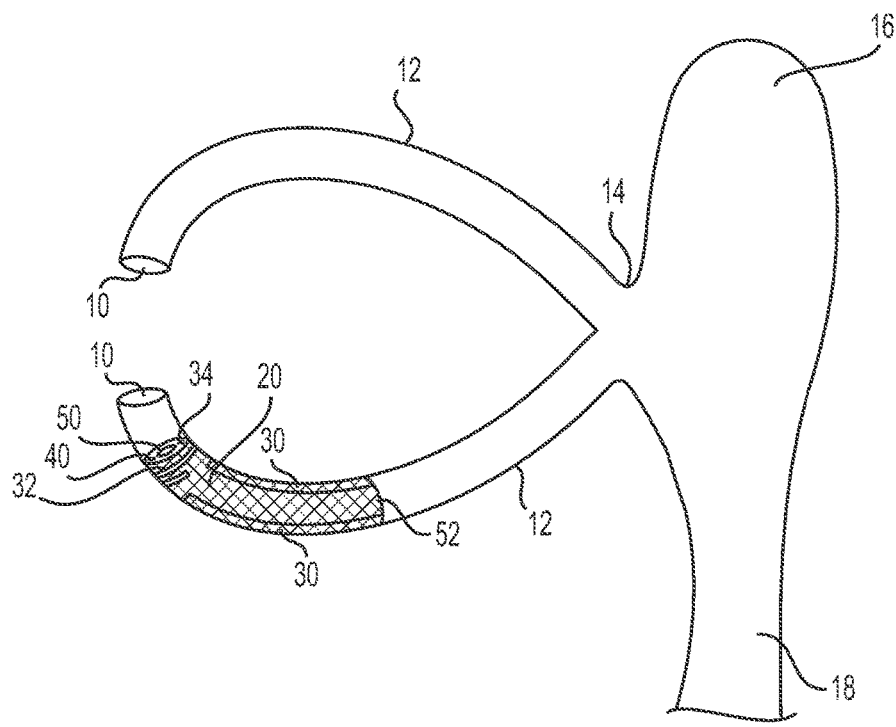
FIG. 10 illustrates the exemplary stimulator of FIG. 9 positioned within the lacrimal system of a subject.

The mesh 52 may comprise any one or more appropriate biocompatible materials, such as, for example, Nitinol or polymer. Optionally, the mesh 52 may be comprised of a conductive material. In such arrangements, separate conductors 30 may not be necessary. Rather, stimulation may be delivered to tissue of the canaliculus 12 through the conductive mesh 52. In some arrangements, the mesh 52 may be self-expanding. That is, upon insertion of the body 20 including mesh 52 within a canaliculus 12, the mesh 52 may expand so as to maintain contact between the conductors 30 and tissue within the canaliculus 12. In other arrangements, the mesh 52 may not be self-expanding. That is, upon deployment within the canaliculus 12, an expansion device (e.g., a balloon) may be inserted within the lumen 50 and expanded (e.g., inflated) so as to expand the mesh 52. In either arrangement, the mesh 52 may urge, push, or otherwise maintain the conductors 30 in contact with tissue so as to increase the efficacy of stimulation. For example, as shown in FIG. 10, the stimulator device of FIG. 9 may be inserted into a canaliculus 12 of the nasolacrimal drainage system. While only a single stimulator device is illustrated within the nasolacrimal drainage system, multiple stimulator devices may be arranged therein. For example, a first stimulator device may be positioned within a canaliculus 12 while a second stimulator device may be positioned within a second canaliculus 12 of the nasolacrimal drainage system. Additionally or alternatively, multiple stimulator devices may be positioned within the same or a common canaliculus 12 of the nasolacrimal drainage system. Although not shown, the stimulator devices of FIG. 8 and FIG. 9 may further include a faceplate 26 as shown in FIGS. 6 and 7.

Figure 11:
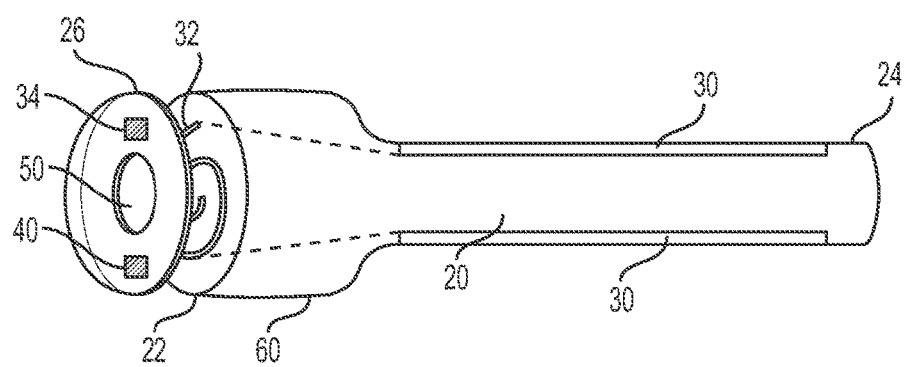
FIGS. 11 and 12 illustrate further exemplary stimulators according to aspects of the current disclosure.
Figure 12:
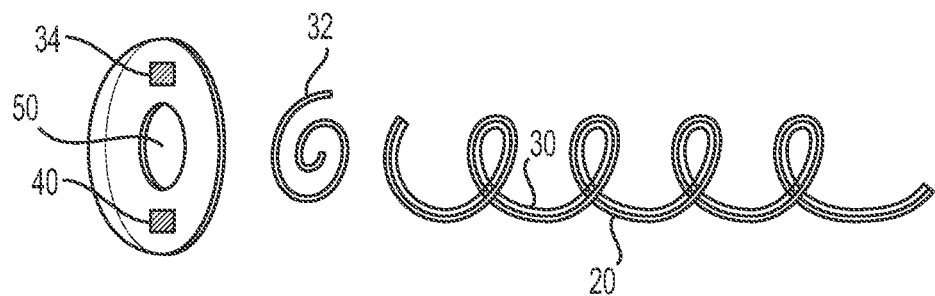

FIG. 11 illustrates an exploded view of a still further arrangement in which the body 20 includes a retention portion 60. The retention portion 60 may be selectively expandable so as to expand to facilitate retention of body 20 within the canaliculus 12. The retention portion 60 may include a balloon or other such expandable member which, upon insertion of a fluid (e.g., air, saline, hydrogel, etc.) through a delivery lumen (not shown), may expand as shown in FIG. 11, to lodge, catch, or otherwise fix the body 20 in place within the canaliculus 12. Optionally, the retention portion 60 may be comprised of a self-expanding material. That is, upon exposure of the retention portion 60 to body heat within canaliculus 12, the retention portion 60 may expand. FIG. 12 illustrates an exploded view of yet an additional arrangement in which the body 20 may include a spring or coil. In some arrangements, the body 20 may be an extension of the coil 32, or may be a discrete member joined to the coil 32. As shown, the conductor 30 may extend along the length of the coil of the body 20. Additionally, in some arrangements, the coil of the body 20 may itself be conductive, thus, eliminating the need for a separate conductor 30.

Figure 13:
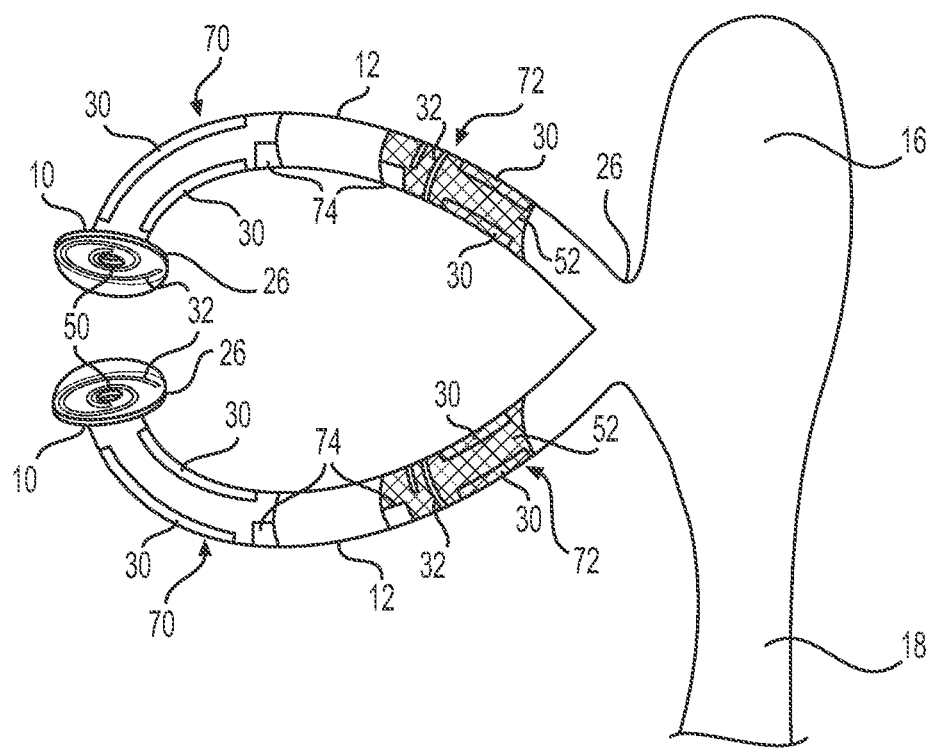
FIG. 13 illustrates a plurality of stimulators positioned within the lacrimal system of the subject.

In a further arrangement, as shown in FIG. 13, a plurality of stimulator devices may be arranged in the nasolacrimal drainage system. For example, two stimulator devices may be arranged in a first canaliculus 12, while an additional two stimulator devices may be arranged in a second canaliculus 12. A first stimulator device 70 within each canaliculus 12 may include a faceplate 26 positioned to abut the puncta 10 of each canaliculus 12. A second stimulator device 72 within each canaliculus 12 may not include faceplate 26. As such, each second stimulator device 72 may be received entirely within a canaliculus 12. As shown in FIG. 13, the first and second stimulator devices 70, 72 may have varied arrangements. For example, first stimulator devices 70 may be similar in construction and function to the stimulator device illustrated in FIG. 7, while second stimulator devices 72 may be similar in construction and function to the stimulator device illustrated in FIG. 9. However, such an arrangement is merely exemplary. In alternative arrangements, each of the first and second stimulator devices 70 and 72 may be the same or different than every other stimulator device.

As shown in FIG. 13, each of first and second stimulator devices 70 and 72 may include a magnet member 74. For example, the first stimulator device 70 in a first canaliculus 12, may include a magnetic member 74 having a pole orientation opposite that of a magnetic member 74 in the second stimulator device 72 in the first canaliculus 12. Similarly, the first stimulator device 70 in a second canaliculus 12, may include a magnetic member 74 having a pole orientation opposite that of a magnetic member 74 in the second stimulator device 72 in the second canaliculus 12. That is, pairs of stimulator devices within a common canaliculus 12 may be attracted to one another to maintain a relative positioning of the first stimulator device 70 relative to the second stimulator device 72. Alternatively, the first stimulator device 70 in a first canaliculus 12, may include a magnetic member 74 having a pole orientation similar to that of a magnetic member 74 in the second stimulator device 72 in the first canaliculus 12. Similarly, the first stimulator device 70 in a second canaliculus 12, may include a magnetic member 74 having a pole orientation similar to that of a magnetic member 74 in the second stimulator device 72 in the second canaliculus 12. That is, pairs of stimulator devices within a common canaliculus 12 may be opposed from one another to maintain a relative spacing of the first stimulator device 70 relative to the second stimulator device 72. In addition, either or both of the first stimulation device 70 or the second stimulation device 72 in the first canaliculus 12 may be coupled (e.g., magnetically) with either or both of the first stimulation device 70 or the second stimulation device 72 of the second canaliculus 12. In such a manner, two stimulation devices 70 or 72 can be inserted at same time and may couple or connect and anchor each other in place.

In order to insert any of the above disclosed stimulator devices of FIG. 4, 5, 6-9, 11, or 12, a user may gather the following items: A punctal dilator, any of the above disclosed stimulator devices, and a suitable forceps. Any appropriate punctal dilator may be used such as, for example, a reusable autoclavable stainless steel dilator. Next, the user may apply a drop of topical anesthetic to the puncta 10 of the subject to numb or dull the sensitivity in the area. Next, the subject may be arranged behind a slit lamp and if necessary, a user may dilate the puncta 10 of the subject. Then, the user may grasp any of the above-described stimulator devices (e.g., via the body 20) with the forceps and insert the distal end 24 into the puncta 10. The user may continue insertion of the stimulator device until either (1) the entirety of the stimulator device is positioned through the puncta 10 and in the canaliculus 12, or (2) until the faceplate 26 (if applicable) abuts the puncta 10. Next, the user may visualize the implanted stimulator device via the slit lamp to ensure proper orientation. If necessary, the user may additionally apply gentle downward pressure on the implanted stimulator device until the faceplate 26 (if applicable) abuts or is flush against the puncta 10. The user then may repeat this process as necessary to insert all required stimulator devices within the nasolacrimal drainage system of a subject. Additionally, in the case of the stimulator device of FIG. 9, if mesh 52 is not a self-expanding mesh, the user may deliver an inflation mechanism (e.g., a balloon) into lumen 50 to expand mesh 52.

In arrangements where the stimulator device includes the lumen 50 (or the lumen 222), an introducer (not shown) may be extended through the lumen 50 (or the lumen 222) towards the distal end 24 (or distal end 103) until an end of the introducer abuts or otherwise engages a portion of the distal end 24 (or the distal end 103), and/or is coupled to the distal end 24 (or the distal end 103). The introducer then may be manipulated so as to stretch or otherwise tension the body 20 (or the body 112) such that a diameter of the body 20 (or the body 112) may be reduced temporarily from a resting state diameter to a reduced caliber diameter. After stretching, the body 20 (or body 112) may be inserted through the puncta 10 and the canaliculus 12. Upon insertion, the insertion device may be uncoupled or removed from the lumen 50 (or the lumen 222) such that body 20 (or body 112) may reassume or expand to its resting state diameter. Such an arrangement may facilitate enhancing contact between the body 20 (or the body 112) and surrounding tissue, as well as enhancing the body 20 (or the body 112) retention within the canaliculus 12. In this arrangement, a user may not be required to dilate the puncta 10.

Further, in some arrangements, a device may be used to test the efficacy of the stimulation dosage prior to implantation of one of the above-described stimulation devices. As such, a probe (not shown) may be operably connected to an energy source (either wirelessly or via a wired connection) and may be positioned in the canaliculus 12. The power source then may be calibrated until a desired tearing response is noted by the subject and/or the user. Such a desired tearing response may be determined either subjectively or through objective measurements including, for example, Schirmer testing or optical coherence tomography imaging of the tear lake.

While previous therapeutic devices are known (see, e.g., U.S. Pat. Nos. 5,713,833; 7,146,209; 8,996,137; and U.S. Patent Application Publication No. 2013/0006326, all of which are incorporated herein by references in their entireties) the devices disclosed herein may exhibit a number of benefits including, for example: 1) Upon implantation or insertion, no portion of the disclosed devices herein enter the nasal cavity or touch the septum; 2) Upon implantation or insertion, the devices disclosed herein may be located completely within the tear drainage system which empties into the nasal cavity but is distinct from the nasal cavity; 3) The disclosed devices may include a proximal end faceplate that may be easily accessible for device removal if needed; 4) The disclosed devices may not require interaction with the subject and can be inserted one time and act for a short or long duration; 5) The disclosed system can be used to analyze the tear film at the level of the faceplate and provide real time feedback for the tear film environment; 6) The system may avoid contact with the vascular nasal cavity and is therefore less likely to cause bleeding, inflammation, and/or discomfort; and 7) The system may treat dry eyes through two separate mechanisms which include blocking outflow of tears from the ocular surface into the tear drainage system and providing stimulus at the level of the nasolacrimal mucosa to produce more tears.

Further discussion of various components of the disclosed examples will now follow below.

User Interface

In instances where the stimulators described herein include a user interface, the user interface may include one or more operating mechanisms, which may allow the user to control one or more functions of the stimulator. For example, the operating mechanisms may allow the user to power the device on or off, start or stop the stimulus, change the intensity of the stimulus, change the duration of the stimulus, change the stimulus pattern, or the like. In one example, the operating mechanisms may be able to activate or deactivate different functions, and/or may be able to change different parameters, based on their manner of operation (e.g., pressing a button briefly, pressing a button for a prolonged period, pressing a button with a particular pattern of pressing actions, rotating a dial by different angles or different speeds). Each of the one or more operating mechanisms may be any suitable structure, such as but not limited to a button, slider, lever, touch pad, knob, or deformable/squeezable portion of the housing, and a stimulator may include any combination of different operating mechanisms.

Additionally or alternatively, in some variations the stimulator body may include a display, which may be configured to convey information to a user via text and/or images. Additionally or alternatively, the stimulator body may include a speaker or buzzer configured to produce one or more speech prompts or other sounds. Additionally or alternatively, the stimulator body may be configured to vibrate. When the stimulator body is configured to vibrate, the duration and/or repetition of the vibration may convey information to the user. It should be appreciated that when the stimulator is configured to deliver a mechanical stimulus (e.g., vibration), as described in more detail below, vibration and/or noise caused by the mechanical stimulus delivery may be used to convey information to the user.

As previously mentioned, a plurality of vibrating elements can be employed according to the instant disclosure. When a plurality of piezoelectric vibrating elements are employed, they should be aligned such that the vibrational waves that they emit do not compress each other or diminish the effects of the waves that one or the others emit. In cases where the vibrating elements are stacked (i.e., contacting each other) those skilled in the art will recognize that the poles of the vibrating elements should be aligned such that positive poles are contacting each other and negative poles are at opposite ends of the stack. On the other hand, if multiple vibrating elements are not stacked, but are spaced from one another, they are preferably spaced from each other at locations on, for example, a shaft where the energy of the waves which they emit is at a minimum. These locations are primarily based upon the wavelength of the waves created by the vibrating elements.

It should be appreciated that while the user interfaces described above are located on the stimulator bodies, in other variations, all of a portion of the user interface of the stimulator may be located on the bio-stimulus transducer. Additionally or alternatively, all or a portion of the user interface may be located on a separate unit, which may be physically or wirelessly attached to the stimulator. For example, in variations where the stimulator is configured to connect to a computer or mobile device (e.g., cellular telephone, tablet, wearable computer (e.g., optical head-mounted displays such as Google Glass™), or the like, as will be discussed in more detail below), the mobile device may act as a user interface. For example, the mobile device may act as a display to convey information to the user or may allow the user to control or program the device.

Control Subsystem

Generally, the control subsystem may be configured to control a stimulus to be delivered to a subject via the bio-stimulus transducer. The control subsystem may be contained within the housing the stimulator. The control subsystem may be connected to the operating mechanisms of the stimulator (e.g., the buttons), which may allow the control subsystem to receive input from a user. The control subsystem also may be connected to mechanisms configured to provide feedback or otherwise convey information to a user.

Additionally or alternatively, the control subsystem may include a communications subsystem. The communication subsystem may be configured to facilitate communication of data and/or energy between the stimulator and an external source. For example, in some variations the communications subsystem may be configured to allow the stimulator to communicate wirelessly (e.g., via Wi-Fi, Bluetooth, or the like) with an external device (e.g., an external programmer, base station, laptop or other computer, mobile device such as a mobile phone, tablet, wearable computer (e.g., optical head-mounted displays such as Google Glass™) or the like), and may include an antenna, coil, or the like. Additionally or alternatively, the communication subsystem may be configured to communicate with an external device (e.g., a flash drive, a laptop or other computer, a mobile device such as a mobile phone, palm pilot, or tablet, or the like) via a wired transmission line. In these variations, the stimulator may include one or more ports (e.g., a USB port), connectors and/or cables configured to physically connect the stimulator to an external device, such that data and/or energy may be transmitted between the stimulator and the external device.

Power Source

The stimulator may include a power source. The power source may be any suitable power supply capable of powering one or more functions of the stimulator, such as one or more batteries, capacitors, or the like. In one example, the power source may be rechargeable. In one example, the rechargeable power source may be recharged wirelessly.

Electrodes

When the stimulators described herein are configured to deliver an electrical stimulus, at least one of the bio-stimulus transducers may include one or more electrodes configured to deliver a stimulus to tissue. In some other variations, for example, an electrode may be ellipsoid or spherical, ovoid, or the like. In yet other variations, the electrodes may include an array of electrodes. In one example, having an array of electrodes may allow a stimulus to be delivered to tissue even if one or more of the electrodes in the array fails, and/or may facilitate unilateral stimulation with a lacrimal system bio-stimulus transducer. When an electrical stimulus is delivered through the electrodes, the stimulation energy may be directed toward the mucosa. This may allow for selective activation of nerves in the mucosa, while minimizing activation of nerves toward collateral areas. The electrode may have any suitable length, such as between about 1 mm and about 10 mm, between about 3 mm and about 7 mm, about 5 mm, or more than about 10 mm.

The electrode(s) described herein may be made from one or more conductive materials. In one example, the electrodes may comprise metals (e.g., stainless steel, titanium, tantalum, platinum or platinum-iridium, other alloys thereof, or the like), conductive ceramics (e.g., titanium nitride), liquids, gels, or the like. In one example, the electrode may comprise one or more materials configured to promote electrical contact between electrodes of the bio-stimulus transducer and tissue (i.e., all of an electrodes or a portion of the electrode, such as a covering). In some instances, the impedance provided by tissue may be at least partially dependent on the presence or absence of fluid-like materials (e.g., mucous) in the lacrimal system. The material(s) may help to minimize the impact of subject tissue impedance by providing a wet interface between the electrode and tissue, which may act to normalize the impedance experienced by the electrodes. This may in turn normalize the output and sensation experienced by the user.

While the bio-stimulus transducers are described in some instances herein with respect to delivery of an electrical stimulus, it should be appreciated that the stimulators described herein may be configured to deliver other types of stimuli, including mechanical, chemical, or other forms of stimulation. In variations in which the stimulators are configured to deliver a mechanical stimulus, the lacrimal system bio-stimulus transducers may be configured to deliver vibrational energy to mucosa of the lacrimal sac and upper region of the nasolacrimal duct. In variations where a stimulator may include one or more bio-stimulus transducers configured to be inserted at least partially into a lacrimal system (such as described herein), the bio-stimulus transducers may be configured to vibrate relative to tissue. In variations where a stimulator is implanted in a nasal or sinus cavity, one or more portions of the stimulator may be configured to vibrate. In one example, the vibration may be generated using one or more magnetic components positioned externally of the body. In these variations, mechanical energy may be used to activate mechanical receptors in afferent neurons.

Additionally or alternatively, the lacrimal system bio-stimulus transducers may be configured to deliver ultrasonic energy to tissue. In these variations, the lacrimal system bio-stimulus transducers (and stimulator bodies) may be configured to have similar physical properties as described herein, although the lacrimal system bio-stimulus transducers need not include electrodes. Instead, the lacrimal system bio-stimulus transducers or the stimulator body may include vibrating motors in variations configured to vibrate all or a portion of the lacrimal system stimulator, or may include one or more ultrasound transducers configured to deliver ultrasonic energy. In one example, the ultrasound transducers may be located in place of the electrodes described herein.

In some other variations, the stimulators described herein may be configured to deliver thermal, light-based, and/or magnetic stimuli. In one example, stimulators may be configured to deliver one or more pulses of air to tissue via the lacrimal system bio-stimulus transducers, which may stimulate tissue. The pulses of air may be generated via a source of compressed air, or the like. In one example, the gas may be warmed or cooled (e.g., mechanically or via one or more thermally-activated fibers). In other variations, the lacrimal system bio-stimulus transducers may be heated or cooled to provide thermal stimulation to tissue. Additionally or alternatively, the stimulator may include one or more light-generating or magnetic field-generating elements, which may be used to stimulate mucosa of the lacrimal sac and upper region of the nasolacrimal duct via the lacrimal system bio-stimulus transducers.

In yet other variations, the bio-stimulus transducers may be configured to deliver one or more chemical agents to mucosa of the lacrimal sac and upper region of the nasolacrimal duct. The chemical agent may be one or more drugs, such as a histamine receptor agonist, nicotinic agonist, or the like. In other variations, the chemical agent may contain one or more irritants, such as ammonia, benzene, nitrous oxide, capsaicin (e.g., propanethial S-oxide), mustard oil, horseradish, crystalline silica, or the like. The lacrimal system bio-stimulus transducers may in these instances include delivery ports for delivering one or more chemical agents, and may additionally include lumens connecting the delivery ports to one or more reservoirs located in the base member of the stimulation bio-stimulus transducer and/or in the stimulator body.

Electrical Connection

Generally, when the stimulators described herein are configured to deliver an electrical stimulus, the electrodes of the stimulator may be electrically connected to the stimulator circuitry, such that the stimulator may generate a stimulus and deliver it to tissue via one or more of the electrodes. Accordingly, the stimulators described herein may include one or more electrical connections configured to electrically connect the electrode via a lead to a portion of the stimulator body (e.g., a stimulation subsystem housed in the stimulator body). In variations in which the bio-stimulus transducer and stimulator body are indirectly connected, the indirect connection (e.g., a cable, cord, or the like) may serve as the electrical connection between the stimulator circuitry and the electrodes. In variations in which the bio-stimulus transducer and the stimulator body are directly connected, the stimulator body and bio-stimulus transducer may include conductive elements configured to electrically connect the electrodes of the bio-stimulus transducer to the stimulator circuitry when the body and bio-stimulus transducer are connected.

Disposable Design

In one example, some portion or all of the stimulator may be disposable. In variations where the stimulator body is permanently attached to the bio-stimulus transducer, the entire stimulator may be disposable. In other variations, one or more portions of the stimulator may be reusable. For example, in variations where the bio-stimulus transducer is releasably connected to the stimulator body, the stimulator body may be reusable, and the bio-stimulus transducer may be disposable. As such, the bio-stimulus transducer may be periodically replaced, such as will be described in more detail below. In yet other variations, a portion of the bio-stimulus transducer section may be disposable (e.g., the bio-stimulus transducer may include disposable sections) and may be periodically replaced. In one example, the stimulators described herein may include features that encourage or require a user to replace a stimulator or stimulator components after a certain period or on a regular basis in order to main proper hygiene.

Additionally or alternatively, in some variations the stimulator may be configured to alert the user and/or enter an inoperable state when a used bio-stimulus transducer is attached to the stimulator body. The stimulator may alert the user in any suitable manner, and may additionally or alternatively be configured to instruct the user to replace the bio-stimulus transducer, as described herein. In these variations, the stimulators may include a mechanism for determining whether the attached bio-stimulus transducer is new (i.e., whether the bio-stimulus transducer has been previously attached to a stimulator body or not). In one example, the mechanism for determining whether the bio-stimulus transducer is new may include a fuse. In one example, the fuse may temporarily short circuit the stimulator circuitry while the bio-stimulus transducer is being connected to the stimulator body.

Additionally or alternatively, the base station may be configured to wirelessly transmit or receive data from the stimulator. In variations where data may be transmitted between the stimulator and the base station, the base station may be configured to provide programming instructions to the stimulator. The base station may be configured to be attached to an external computing device, to transfer data downloaded from the stimulator and/or receive programming instructions to be provided to the stimulator. In variations where the base station may include a port (such as a USB port), the port may be used to attach the base station to an external computing device.

External Device Connection

In some variations the stimulators described herein may be configured to connect to an external device, such as a mobile device (e.g., a cellular telephone, a tablet, a wearable computer (e.g., optical head-mounted displays such as Google Glass™), or the like), a computer, or the like. The stimulators may be configured to connect to an external device through any suitable connection method. In some variations the connection method may be wireless (e.g., via Wi-Fi, Bluetooth, or the like), and the stimulator may include an antenna or the like. In one example, the device may be programmed via a program application or "app" on an external device. In one example, the device may be operated in a real time operation with a connection to an external device by way of communication through the device antenna. Additionally or alternatively, the connection method may be via a wired transmission line. In these variations, the stimulator may include one or more ports (e.g., a USB port), connectors and/or cables configured to physically connect the stimulator to an external device. In one example, the stimulators may use a wireless or wired connection to connect to the internet, via which they may be connected to an external device. In these variations, the device may be at a distant location (e.g., at the manufacturer, at a physician's office, or the like).

In instances in which the stimulators are configured to connect to an external device, the device may be configured to perform one or more operations associated with the stimulator. For example, in variations where the stimulator is configured to collect data (e.g., one or more subject parameters, stimulation timing or parameters, stimulator diagnostic information, such as described in more detail herein) and store that data in a memory unit of the stimulator, connection of the stimulator to the device may allow for transfer of data stored in the stimulator's memory unit to the device. Specifically, the device and stimulator may be programmed such that upon connection of the device and the stimulator, the device may download the recorded data stored in the stimulator's memory. In one example, once data has been transferred from the stimulator to the device, the stimulator may be configured to delete this data from the stimulator memory. Because the amount of memory available in the device may be greater than that in the stimulator, this transfer may increase the data that may be accumulated for a subject.

In addition to or instead of transferring data stored in the stimulator memory, a device may be configured to collect and store real-time data from the stimulator when the two are connected. In one example, the stimulator also may be configured to store this data in the stimulator memory. In some instances, the device may be configured to transmit data (e.g., via internet connection, cellular data network, or the like) from the device to an external location (e.g., to a database where the data may be analyzed, to a physician's office to allow the physician to monitor the data and, in some instances, provide feedback).

In one example, the device may be configured to solicit input from a user. For example, if the stimulator is used to provide stimulation while attached to a device, the device may be configured to solicit the user to input data regarding the subject's experience (e.g., a subject's level of comfort/discomfort, status of subject's symptoms). In one example, the device may be configured to present data (and/or analysis of the data) to a user. For example, the device may be configured to display information regarding the frequency of stimulation, the average duration of stimulation, a graph of subject comfort levels over time, or the like. In one example, the device may be configured to share the data or analysis of the data with the manufacturer, clinicians, friends, or others.

Implantable Stimulators

In some variations of the stimulation systems described here, the stimulation system may include a stimulator configured to be implanted, either permanently or temporarily, in a subject. It should be appreciated that the implantable stimulators need not be surgically implanted. In some of these instances, the implantable stimulator may be configured such that the stimulator may be inserted and/or removed by a user. In others of these instances, the implantable stimulator may be configured to be inserted and/or removed by a medical professional. In other instances, the stimulator may be configured to be implanted in or otherwise attached to tissue within a nasal or sinus cavity.

In still other variations, the stimulation systems described herein may include a stimulator that is configured to be implanted within or beneath mucosal tissue. The stimulator may be implanted in a nasal or sinus cavity, and may be placed within the mucosa, beneath the mucosa, between mucosa and bone and/or cartilage, within the cartilage, or the like. Generally, the stimulator may include a stimulator body and one or more electrodes, and may include any of the stimulators described in U.S. Patent Application Publication No. 2013/0006326 A1, filed on Apr. 6, 2012, and titled "Stimulation devices and methods," which was previously incorporated by reference in its entirety.

Device Insertion

While not limiting the current disclosure, one method of insertion of the device would be to introduce the unexpanded device on the punctal side in an insertion method similar to the introduction of a Crawford tube. In one example, the expandable distal end of the device is envisioned to fit through the punctum and canaliculus wherein the reservoir of the device would reside in the lacrimal sac allowing for potential expansion to conform to anatomical features. In one example, the proximal end faceplate rests upon the punctum. In one example, a lubricant is coupled with the system to allow for smoother atraumatic insertion. While not limiting the device, it is envisioned that the device would conform the standard anatomical size variations. In one example, the device could be used for subjects of various sizes and age ranges. In one example, the device may not be appropriate in certain subjects, including, but not limited to subjects with trauma to the nasolacrimal system, subjects with chronic nasal inflammation, or dacryocystitis. Dacryocystitis is an inflammation of the lacrimal sac, frequently caused by nasolacrimal duct obstruction or infection. In one example, the device functions and serves for at least two months or greater than sixty days. In the particular cases of treating dye eye, the device therapy would last at least two months.

Stimulation Methods

Generally, the stimulators and stimulation systems described herein may be configured to stimulate mucosa of the lacrimal sac and upper region of the nasolacrimal duct. In one example, the stimulation may be used to cause tear production by a user. Generally, a stimulator (such as described above) may be configured to stimulate one or more nasal or sinus afferents which may activate a lacrimation response via a nasolacrimal reflex. In some instances, this may include stimulating one or more branches of the trigeminal nerve or trigeminal nerve afferents. In some of these instances, this may include stimulating the ophthalmic 96 branch of the trigeminal nerve. This stimulation may be used to treat various forms of dry eye, including (but not limited to), chronic dry eye, episodic dry eye, seasonal dry eye, aqueous deficient dry eye, or evaporative dry eye.

In some instances, the stimulation may be used as a prophylactic measure to treat users which may be at an increased risk of developing dry eye, such as subjects who will undergo or who have undergone ocular surgery such as refractive vision correction and/or cataract surgery. In other instances, the stimulators may be used to treat ocular allergies. For example, an increase in tear production may flush out allergens and other inflammatory mediators from the eyes. In some instances, the stimulation delivered by the stimulators described herein may be configured to cause habituation of the neural pathways that are activated during an allergic response (e.g., by delivering a stimulation signal continuously over an extended period of time). This may result in reflex habituation which may suppress the response that a user would normally have to allergens.

Location

When an implantable stimulator is used to provide stimulation, the implantable stimulator may be positioned in a nasal or sinus cavity (or multiple nasal or sinus cavities). When a stimulator is used to provide stimulation, one or more lacrimal system bio-stimulus transducers of the stimulator may be activated in the lacrimal system of a user, and a stimulation signal (such as described above) may be delivered to the mucosal tissue.

A portion of the lacrimal system bio-stimulus transducer(s) may be positioned and/or manipulated to be placed in contact with any suitable tissue. (In variations in which the stimulators are configured to deliver an electrical stimulus, the stimulators may be positioned and/or manipulated to position electrodes into contact with any suitable tissue.) For example, the lacrimal system bio-stimulus transducer(s) may be placed in contact with the tear drainage system or nasolacrimal mucosa or the like. When the stimulators are used to produce a tearing response as discussed herein, it may be desirable to position a portion of the bio-stimulus transducers (e.g., an electrode) in contact with the lacrimal system mucosa. In some instances, the targeted area may include tissue innervated by the infratrochlear nerve. In some instances, the targeted area of the lacrimal system mucosa may be between the punctum and the nasolacrimal duct. In one example, it may be desirable to place a portion of the bio-stimulus transducer(s) (e.g., an electrode) between about 0.5 mm and about 30 mm into the tear drainage system of the subject. As described herein, it may in some instances be desirable to direct the bio-stimulus transducer such that a portion (e.g., the electrodes) is directed toward the lacrimal sac and duct. Avoiding stimulation of the septal nerves and surrounding nerves is desirable so as to reduce negative side effects that may occur from inadvertent stimulation of the olfactory area.

Electrical Stimulus

In one example, the stimulation may be delivered unilaterally (e.g., in a single nostril). For example, in variations where a stimulator may include a single bio-stimulus transducer, the bio-stimulus transducer may be placed in a through one punctum and into the lacrimal system, and stimulation may be delivered to the lacrimal system via the bio-stimulus transducer. It should be appreciated that in some of these variations in which the stimulus is electrical, an electrode or other return electrode may be affixed to or otherwise be placed in contact an anatomical area external to the lacrimal system a return electrode. In one example, such external connection to the electrode may be used in a testing phase of the device, post implantation. In some variations where a stimulator may include two or more bio-stimulus transducers, each of the bio-stimulus transducers may be placed in a first punctum per eye, and some or all of the bio-stimulus transducers may be used to deliver stimulation to mucosal tissue. In other variations where a stimulator may include two or more bio-stimulus transducers, at least one bio-stimulus transducer may be positioned in a first punctum per eye, and at least one bio-stimulus transducer may be positioned in the second punctum per eye. In some examples, each eye may have two devices implanted into each lacrimal system. In one example, each punctum of the eye may contain one implanted medical device. In variations in which the stimulus is electrical, some or all of the bio-stimulus transducers in each lacrimal system may be used to deliver unilateral electrical stimulation to each lacrimal system (e.g., the bio-stimulus transducer(s) in each lacrimal system may remain independently inactive).

In one example, the stimulators may be used to provide bilateral stimulation of the lacrimal system mucosal tissue. In these variations, at least one stimulator device including a bio-stimulus transducer may be positioned in a first lacrimal system and at least one stimulator device including a bio-stimulus transducer may be positioned in a second lacrimal system. In these variations, when the stimulus is electrical, electrical stimulation may be delivered between the bio-stimulus transducer in the first lacrimal system and the bio-stimulus transducer of the second lacrimal system, which may cause current to flow between the two devices.

Electrical Stimulus: Waveforms

When the stimulus is electrical, the electrical stimulus delivered by the stimulators described herein may include a waveform or waveforms, which may be tailored for specific treatment regimens and/or specific subjects. The waveforms may be pulse-based or continuous. It should be appreciated that the waveforms described herein may be delivered via a bipolar configuration or a monopolar configuration. When the stimulator is configured to deliver a continuous waveform, the waveform may be a sinusoidal, quasi-sinusoidal, square-wave, saw tooth/ramped, or triangular waveform, truncated-versions thereof (e.g., where the waveform plateaus when a certain amplitude is reached), or the like. Generally, the frequency and peak-to-peak amplitude of the waveforms may be constant, but in some variations the stimulator may be configured to vary the frequency and/or amplitude of the waveform. This variation may occur according to a pre-determined plan, or may be configured to occur randomly within given parameters. For example, in some variations the continuous waveform may be configured such that the peak-to-peak amplitude of the waveform varies over time (e.g., according to a sinusoidal function having a beat frequency). In some instances varying the amplitude and/or frequency of a stimulation waveform over time, or pulsing the stimulus on and off (e.g., 1 second on/1 second off, 5 seconds on/5 seconds off), may help reduce subject habituation (in which the subject response to the stimulation decreases during stimulation). Additionally or alternatively, ramping the amplitude of the stimulation waveform at the beginning of stimulation may increase comfort.

When the stimulator is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). In one example, it may be desirable to configure the biphasic pulse to be charge-balanced, so that the net charge delivered by the biphasic pulse is approximately zero. In one example, a biphasic pulse may be symmetric, such that the first phase and the charge-balancing phase have the same pulse width and amplitude. Having a symmetric biphasic pulse may allow the same type of stimulus to be delivered to each lacrimal system. The pulses of a first phase may stimulate a first side of the nose (while providing a charge-balancing phase to a second side of the nose), while the pulses of the opposite phase may stimulate the second side of the nose (while providing a charge-balancing phase to the first side of the nose). In other variations, a biphasic pulse may be asymmetric, where the amplitude and/or pulse width of the first pulse may differ from that of the charge-balancing phase. Additionally, each phase of the biphasic pulse may be either voltage-controlled or current-controlled. In one example, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa.

In variations where the waveform may include a biphasic pulse, the biphasic pulse may have any suitable frequency, pulse widths, and amplitudes. For example, in instances where the stimulators described herein are used to treat dry eye or otherwise produce a tearing response by stimulating mucosa of the lacrimal sac and upper region of the nasolacrimal duct, the stimulator may be configured to generate a biphasic pulse waveform at a frequency between about 0.1 Hz and about 200 Hz. In one example, the frequency is preferably between about 10 Hz and about 60 Hz. In one example, the frequency is preferably between about 25 Hz and about 35 Hz. In one example, the frequency is preferably between about 50 Hz and about 90 Hz. In one example, the frequency is preferably between about 65 Hz and about 75 Hz. In other variations, the frequency is preferably between about 130 Hz and about 170 Hz. In one example, the frequency is preferably between about 145 Hz and about 155 Hz. In one example, high frequencies, such as those between about 145 Hz and about 155 Hz may be too high for each pulse to stimulate/activate the target nerves. As a result, the stimulation may be interpreted by the patient to have an element of randomness, which in turn may help to reduce subject habituation.

Similarly, for the treatment of dry eye, the when the stimulus is electrical and the first phase of the biphasic pulse is current-controlled, the first phase may preferably have an amplitude between about 10 μA and 100 mA. In one example, the amplitude may be preferably between about 0.1 mA and about 10 mA. When the first phase of the biphasic pulse is voltage-controlled, the first phase may preferably have an amplitude between about 10 mV and about 100 V. Additionally, the first phase may preferably have a pulse width between about 1 μs and about 10 ms. In one example, the pulse width may preferably be between about 10 μs and about 100 μs. In other variations, the pulse width may preferably be between about 100 μs and about 1 ms.

When an electrical pulse waveform is an alternating monophasic pulsed waveform, each pulse delivered by the stimulator may have a single phase, and successive pulses may have alternating polarities. Generally, the alternating monophasic pulses are delivered in pairs at a given frequency (such as one or more of the frequencies listed above, such as between 30 Hz and 50 Hz), and may have an inter-pulse interval between the first and second pulse of the pair (e.g., about 100 μs, between 50 μs and 150 μs or the like). Each pulse may be current-controlled or voltage-controlled, and consecutive pulses need not be both current-controlled or both voltage-controlled. In some variations where the pulse waveform is charged-balanced, the waveform may include e a passive charge-balancing phase after delivery of a pair of monophasic pulses, which may allow the waveform to compensate for charge differences between the pulses.

When a stimulator configured to deliver an electrical stimulus is positioned to place an electrode on either side of the nasal septum, alternating monophasic pulses may promote bilateral stimulation of mucosa of the lacrimal sac and upper region of the nasolacrimal duct. The pulses of a first phase may stimulate a first side of the nose (while providing a charge-balancing phase to a second side of the nose), while the pulses of the opposite phase may stimulate the second side of the nose (while providing a charge-balancing phase to the first side of the nose), since nerves may respond differently to anodic and cathodic pulses. The inter-pulse interval may give time for the stimulation provided by a first phase pulse to activate/polarize the target nerves prior to be reversed by an opposite phase pulse.

When a stimulator is configured to deliver a pulse-based waveform, the stimulation amplitude, pulse width, and frequency may be the same from pulse to pulse, or may vary over time. For example, In one example, the amplitude of the pulses may vary over time. In one example, the amplitude of pulses may vary according to a sinusoidal profile. In one example, the stimulation waveform may be a modulated high frequency signal (e.g., sinusoidal), which may be modulated at a beat frequency of the ranges described above. In such variations, the carrier frequency may be between about 100 Hz and about 100 kHz. In other variations, the amplitude of pulses may increase (linearly, exponentially, etc.) from a minimum value to a maximum value, drop to the minimum value, and repeat as necessary. In one example, the user may be able to control the stimulus during its delivery. After the device has been portioned with bio-stimulus transducer(s) (e.g., the electrode or electrodes) in contact with the mucosa of the lacrimal sac and upper region of the nasolacrimal duct, the user may increase the intensity of the stimulus via a remote operation system. It may be desirable for the patient to increase the intensity of the stimulus until the stimulus causes paresthesia (e.g., tingling, tickling, prickling). As such, the patient may be able to self-determine the proper stimulation intensity and self-adjust the stimulus to a level effective to achieve the desired result (e.g., tear production). It may be desirable for the user to increase the intensity of the stimulus slowly in order to minimize discomfort.

In some instances, it may be desirable to configure the stimulation waveform to minimize side effects. In some instances, it may be desirable to promote stimulation of larger-diameter nerves (e.g., afferent fibers of the trigeminal nerve), which may promote a therapeutic effect, while reducing the stimulation of smaller nerves (e.g., a-delta fibers, c fibers, sympathetic and parasympathetic fibers), which may result in pain, discomfort, or mucus production. One way to avoid these fibers is to directly stimulate the mucosa in the lacrimal sac while avoiding the nasal cavity and septum. Generally, for smaller pulse-widths, the activation threshold for larger-diameter nerves may be lower than the activation threshold for the smaller nerve fibers. Conversely, for larger pulse-widths, the activation threshold for larger-diameter nerves may be higher than the activation threshold for the smaller nerve fibers. Accordingly, in some instances, it may be desirable to select a pulse width that preferably actuations the larger-diameter nerves. In one example, the pulse width may be between 30 µs and about 70 µs, or may be between about 30 µs and about 150 µs.

It should be appreciated that the electrical stimulation devices and systems described herein may be used for one or more diagnostic functions, to modulate blood flow (e.g., to treat headaches), to promote healing, or the like. Additionally, the stimulation systems, devices, and methods described are herein are intended for use with human users, it should be appreciated that they may be modified for veterinary use.

Chemical Stimulus

In one example, one or more chemical agents may be delivered to mucosa of the lacrimal sac and upper region of the nasolacrimal duct to treat one or more conditions. For example, In one example, one or more chemical agents may be used to treat dry eye or otherwise promote a tear-producing response. In one example, the chemical agent may be configured to promote trigeminal nerve activation. The chemical agent may be delivered in any suitable manner. In one example, the chemical agent may be delivered via a stimulator as described herein. In other variations, the chemical agent may be delivered via one or more eye drops (which may drain through the device into the lacrimal system). The chemical agent may include one or more of the agents described above.

Mechanical, Thermal, Light-Base, and Magnetic Stimulus

As mentioned above, in some variations the stimulation systems described herein may be used to provide mechanical, thermal, light-based and/or magnetic stimulation. In one example, a stimulator may be used to deliver vibrational energy to mucosa of the lacrimal sac and upper region of the nasolacrimal duct. In variations where a stimulator may include one or more bio-stimulus transducers configured to be inserted a lacrimal system (such as the electrical stimulators described herein) and made to vibrate. In variations where a stimulator is implanted in a lacrimal system, one or more portions of the stimulator may vibrate while implanted. In one example, the vibration may be generated using one or more magnetic components positioned externally of the body.

Additionally or alternatively, ultrasonic energy may be delivered to tissue by a stimulator including one or more ultrasound transducers. In variations in which stimulators are configured to deliver one or more pulses of air to tissue, one or more pulses of air may be delivered to stimulate tissue. The pulses of air may be generated via a source of compressed air, or the like. In one example, the gas may be warmed or cooled (e.g., mechanically or via one or more thermally-activated fibers). In other variations, one or more portions of a stimulator may be heated or cooled to provide thermal stimulation to tissue. In variations where a stimulator may include one or more bio-stimulus transducers configured to be implanted with a lacrimal system, the stimulator may controllably heat or cool the bio-stimulus transducer. Additionally or alternatively, a stimulator may use one or more light-generating or magnetic field-generating elements to stimulate mucosa of the lacrimal sac and upper region of the nasolacrimal duct.

Treatment Regimens

The stimulation methods described herein may be delivered according to one or more treatment regimens to treat a condition. For example, to treat dry eye, stimulation may be delivered to a subject as-needed and/or according to a pre-determined regimen. In some instances, a user may use one of the stimulation devices described herein to provide a round of stimulation when the user experiences symptoms of dry eye. A round of stimulation may have any suitable duration (e.g., between 0.1 second and 10 minutes).

In other instances, the devices may be used to provide stimulation on a scheduled basis. For example, in some variations the stimulation devices described herein may be used to provide a round of stimulation at least once daily, at least once weekly, or the like. In one example, the stimulation devices may be used to deliver multiple rounds of stimulation each day (e.g., at least two treatments daily, at least three treatments daily, at least four treatments daily, at least five treatments daily, at least six treatments daily, at least seven treatments daily, at least eight treatments daily, between two and ten times daily, between four and eight times daily, or the like). In one example, the stimulation may be delivered at certain times of day. In other variations, the stimulation may be delivered at any time during the day as desired or determined by the user. When the device is used to provide stimulation on a scheduled basis, in some variations each round of stimulation may be the same length (e.g., about 30 seconds, about 1 minute, about 2 minutes, about 3 minutes, about 4 minutes, about 5 minutes, about 10 minutes, or longer than 10 minutes). In other variations, some rounds of stimulation may have different predetermined lengths. In yet other variations, the user may choose the length of the round of stimulation. In one example, the user may be given a minimum stimulation time (e.g., about 5 seconds, about 10 seconds, about 30 seconds, about 1 minute, about 2 minutes, about 3 minutes, about 5 minutes, or the like) and/or a maximum stimulation time (e.g., about 1 minute, about 2 minutes, about 3 minutes, about 5 minutes, about 10 minutes, about 20 minutes, or the like). In some instances, the delivery schedule or stimulation parameters may be changed based on the time of day (e.g., daytime use vs. nighttime use). In one example, the stimulator may include (e.g., as part of a control subsystem) one or more counters and intelligence (e.g., a microcontroller, programmable logic (e.g., a field-programmable gate array), or application-specific integrated circuit (ASIC)). A counter may count oscillator pulses until a certain number have passed, at which point stimulation may be activated. Additionally or alternatively, a counter may measure the duration of stimulation and the intelligence may control the stimulation length. In some examples, the stimulation may follow a custom activation pattern programmed by an external device via wireless communication.

In some examples, the stimulation may be delivered on a continuous basis. When an implantable stimulator is used to deliver stimulation non-continuously as discussed herein, the implantable stimulator may be configured to deliver stimulation automatically or may be configured to deliver stimulation on command. For example, in some variations the stimulator may be configured to deliver stimulation on a pre-programmed basis (e.g., according to a treatment regimen as discussed herein). In other variations, the stimulator may include one or more sensors, and may be configured to deliver stimulation upon detecting a pre-determined condition with the one or more sensors. For example, In one example, a stimulator may include a wetness sensor, and may be configured to deliver stimulation when the wetness sensor registers a certain dry condition in a nasal or sinus cavity. When an implanted stimulator is activated by a user, an external controller may be used (e.g., via a wireless signal such as Bluetooth, near-field RF, far-field RF, or the like) to activate the implanted stimulator.

Treatment Effects

In one example, the treatment regimens described herein may be used to treat dry eye. Current treatment options for dry eye are limited, and they generally provide limited symptom relief or improvement in ocular health. In contrast to current treatment options, the treatment regimens using the stimulators described herein may provide rapid and marked relief and improvement in ocular health, as measured by numerous indicators, including tear production, patient symptoms, and corneal and conjunctival staining. Both the speed and magnitude of relief and improvement in ocular health that may be achieved is surprising given the much slower and more limited ability to treat dry eye with existing treatments. In one example, the treatment regimens of providing the stimuli described herein may cause periodic or regular activation of the nasolacrimal reflex, which may in turn treat dry eye and/or improve ocular health. Periodic or regular activation of the nasolacrimal reflex may improve ocular health by several mechanisms of action. For example, the activation of the nasolacrimal reflex may cause tearing, which in turn may deliver growth factors contained in the tears to the ocular surface. These growth factors include epidermal growth factor (EGF). EGF is a polypeptide that stimulates the growth of various tissues, including the cornea, conjunctiva, and goblet cells. In patients with dry eye, the cornea may become damaged due to desiccation and inflammation; EGF may thus play a role in stimulating the healing process for the cornea. Periodic or regular activation of the nasolacrimal reflex also may improve ocular health by increasing resting tear production, which may promote chronic hydration of the ocular surface, as well as by causing periodic or regular significant increases in tear production during activation. Activation of the nasolacrimal reflex also may improve ocular health by causing vasodilation, which may in turn promote ocular health.

In some examples, an antimicrobial coating can be disposed on, or impregnated in, at least a portion of the outer surface of the implant body to further prevent microbial growth on the implant body. In an example, the antimicrobial coating can include an agent selected from the group including 2-bromo-2-nitropropane-1,3-diol, 5-bromo-5-nitro-1,3-dioxane, 7-ethyl bicyclooxazolidine, benzalkonium chloride, benzethonium chloride, benzoic acid, benzyl alcohol, boric acid, bronopol, cetylpyridinium chloride, chlorhexidine digluconate, chloroacetamide, chlorobutanol, chloromethyl isothiazolinone and methyl isothiazoline, dimethoxane, dimethyl oxazolidine, dimethyl hydroxymethyl pyrazole, chloroxylenol, dehydroacetic acid, diazolidinyl urea, dichlorobenzyl alcohol, DMDM hydantoin, ethyl alcohol, formaldehyde, glutaraldehyde, hexachlorophene, hexetidine, hexamethylenetramine, imidazolidinyl urea, iodopropynyl butylcarbamate, isothiazolinones, methenammonium chloride, methyldibromo glutaronitrile, MDM hydantoin, minocycline, ortho phenylphenol, p-chloro-m-cresol, parabens (butylparaben, ethylparaben, methylparaben), phenethyl alcohol, phenoxyethanol, piroctane olamine, polyaminopropyl biguanide, polymethoxy bicyclic oxazolidine, polyoxymethylene, polyquaternium-42, potassium benzoate, potassium sorbate, propionic acid, quaternium-15, rifampin, salicylic acid, selenium disulfide, sodium borate, sodium iodate, sodium hydroxymethylglycinate, sodium propionate, sodium pyrithione, sorbic acid, thimerosal, triclosan, triclocarban, undecylenic acid, zinc phenosulfonate, and zinc pyrithione. In an example, the antimicrobial coating can include a material selected from the group comprising silver lactate, silver phosphate, silver citrate, silver acetate, silver benzoate, silver chloride, silver iodide, silver iodate, silver nitrate, silver sulfadiazine, silver palmitate or one or more mixtures thereof. In an example, the antimicrobial coating can include at least one of an antibiotic or an antiseptic. For instance, the antimicrobial coating can include a temporary anesthetic lasting, on average, between a few hours and a day. In still other examples, the antimicrobial coating can include a drug use to treat an underlying disease, such as a bolus for immediate effect.

Each of the arrangements disclosed herein may include one or more of the features described in connection with any of the other disclosed arrangements. The foregoing description is exemplary and explanatory only and are not restrictive of the features. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

While principles of the present disclosure are described herein with reference to illustrative arrangements for particular applications, it should be understood that the disclosure is not limited thereto. Those having ordinary skill in the art and access to the teachings provided herein will recognize additional modifications, applications, aspects, and substitution of equivalents all fall within the scope of the arrangements described herein. Accordingly, the disclosure is not to be considered as limited by the foregoing description.

The invention claimed is:

1. A device for inducing production of tears, comprising:
   a body extending from a proximal end to a distal end, wherein the body is configured for insertion through a punctum of a subject;
   a stimulus delivery mechanism positioned between the proximal end and the distal end; and
   a faceplate adjacent the proximal end of the body, the faceplate including a power receptor at least partially disposed therein or thereon;
   wherein the faceplate abuts, and is located external to, the punctum when the body is inserted through the punctum;
   wherein, upon transfer of energy from an external device to the power receptor, tissue of a nasolacrimal drainage system of the subject is stimulated by the stimulus delivery mechanism to induce the production of tears.

2. The device of claim 1, wherein the stimulus delivery mechanism includes a conductor.

3. The device of claim 2, further including a plurality of conductors positioned between the proximal end and the distal end of the body.

4. The device of claim 1, wherein the power receptor is operably coupled to the stimulus delivery mechanism.

5. The device of claim 1, wherein the body is configured for direct contact with a portion of a nasolacrimal drainage system of a subject.

6. The device of claim 1, further including a sensor configured for sensing one or more of biochemical properties of tears, placement of the body, and operation of the stimulus delivery mechanism.

7. The device of claim 6, wherein the sensor is configured to detect a degree of conductivity in a nasolacrimal duct of the subject.

8. The device of claim 1, wherein the power receptor is a coil.

9. The device of claim 1, wherein the stimulus delivery mechanism comprises multiple zones, each of which includes an electrode.

10. The device of claim 9, further comprising:
    a first electrode arranged about the circumference of the body at a first axial location; and
    a second electrode, which is axially spaced apart from the first electrode and arranged about the circumference of the body at a second axial location.

11. The device of claim 1, wherein the power receptor is disposed in or on the faceplate.

12. The device of claim 1, wherein the power receptor comprises a photo-active material.

13. A device for inducing production of tears, comprising:
    a body extending from a proximal end to a distal end, wherein the body is configured for insertion within a portion of a nasolacrimal drainage system of a subject;
    a stimulus delivery mechanism positioned between the proximal end and the distal end;
    a power receptor operably coupled to the stimulus delivery mechanism;
    a faceplate adjacent the proximal end of the body, the power receptor being at least partially disposed within or on the faceplate; and
    an external controller coupled to the power receptor for transferring energy to the power receptor;
    wherein the faceplate abuts, and is located external to, the punctum when the body is inserted through the punctum;
    wherein, upon transfer of energy from an external device to the power receptor, tissue of a nasolacrimal drainage system of the subject is stimulated by the stimulus delivery mechanism to induce the production of tears.

14. The device of claim 13, wherein the body includes an opening extending through a side wall of the body.

15. The device of claim 14, wherein at least a portion of the stimulus delivery mechanism is positioned within the opening.

16. The device of claim 14, wherein the body includes a plurality of openings extending through a side wall of the body.

17. The device of claim 13, wherein the stimulus delivery mechanism includes a conductor.

18. The device of claim 17, further including a plurality of conductors positioned between the proximal end and the distal end of the body.

19. The device of claim 13, wherein the body and the faceplate include non-planar surfaces.

20. The device of claim 13, wherein the body is tapered such that the proximal end has a proximal end diameter and the distal end has a distal end diameter, wherein the distal end diameter is smaller than the proximal end diameter.

21. The device of claim 13, further including a lumen extending from the proximal end of the body to the distal end of the body.

22. The device of claim 13, wherein the body comprises a self-expandable mesh.

23. The device of claim 13, further including a sensor configured for sensing one or more of biochemical properties of tears, placement of the body, and operation of the stimulus delivery mechanism.

24. The device of claim 23, wherein the sensor is configured to detect a degree of conductivity in a nasolacrimal duct of the subject.

25. The device of claim 13, wherein the power receptor is disposed in or on the faceplate.

26. A device for inducing production of tears, comprising:
    a body extending from a proximal end to a distal end, wherein the body is configured for insertion through a punctum of a subject;
    at least two stimulus delivery mechanisms that are positioned between the proximal end and the distal end, the at least two stimulus delivery mechanisms extending at least partially around a portion of the body;
    wherein the at least two stimulus delivery mechanisms are axially spaced apart so that the at least two stimulus delivery mechanisms straddle an area of a canaliculus or a nasolacrimal duct where neural innervation is the greatest, as compared to the rest of the canaliculus or nasolacrimal duct, when the body is inserted through the punctum;
    a power receptor operably coupled to one or more of the at least two stimulus delivery mechanisms; and
    a faceplate adjacent the proximal end of the body, the faceplate including the power receptor at least partially disposed therein or thereon;
    wherein, upon transfer of energy from an external device to the power receptor, tissue of a nasolacrimal drainage system of the subject is stimulated by one or both of the stimulus delivery mechanisms to induce the production of tears.

27. The device of claim 26, wherein the at least two stimulus delivery mechanisms are axially spaced apart at a distance sufficient to excite at least one of a supratrochlear nerve and a infratrochlear nerve when a stimulation signal is applied to a tissue of a nasolacrimal drainage system of the subject via one or both of the at least two stimulus delivery mechanisms.

28. The device of claim 26, wherein the power receptor is disposed in or on the faceplate.

* * * * *